(12) United States Patent
Omenetto et al.

(10) Patent No.: US 9,016,875 B2
(45) Date of Patent: Apr. 28, 2015

(54) ALL-PROTEIN IMPLANTABLE, RESORBABLE REFLECTORS

(75) Inventors: Fiorenzo Omenetto, Wakefield, MA (US); David L. Kaplan, Concord, MA (US)

(73) Assignee: Tufts University/Trustees of Tufts College, Medford, MA (US)

( * ) Notice: Subject to any disclaimer, the term of this patent is extended or adjusted under 35 U.S.C. 154(b) by 48 days.

(21) Appl. No.: 13/386,388

(22) PCT Filed: Jul. 20, 2010

(86) PCT No.: PCT/US2010/042585
§ 371 (c)(1),
(2), (4) Date: Apr. 6, 2012

(87) PCT Pub. No.: WO2011/046652
PCT Pub. Date: Apr. 21, 2011

(65) Prior Publication Data
US 2012/0188640 A1    Jul. 26, 2012

Related U.S. Application Data

(60) Provisional application No. 61/226,801, filed on Jul. 20, 2009.

(51) Int. Cl.
*G02B 5/124* (2006.01)
*A61B 5/00* (2006.01)
*A61L 27/22* (2006.01)

(52) U.S. Cl.
CPC ............. *A61B 5/0059* (2013.01); *A61L 27/227* (2013.01)
USPC ........... 359/530; 359/546; 359/831; 359/838; 359/896

(58) Field of Classification Search
CPC .......................... A61B 5/0059; A61L 27/227
USPC ........ 359/530, 546, 547, 551, 552, 558, 572, 359/831, 838, 896, 900
See application file for complete search history.

(56) References Cited

U.S. PATENT DOCUMENTS 4,676,640 A    6/1987 Briggs
5,245,012 A    9/1993 Lombari et al.
(Continued)

FOREIGN PATENT DOCUMENTS

EP    0245509 A1    11/1987
EP    1116987 A2    7/2001
(Continued)

OTHER PUBLICATIONS

Machine Translation of JP 09-230,177 A, downloaded from http://www.ipdl.inpit.go.jp/homepg_e.ipdl on Dec. 8, 2013.*
(Continued)

*Primary Examiner* — Frank Font
(74) *Attorney, Agent, or Firm* — Choate Hall & Stewart, LLP

(57) ABSTRACT

The invention provides for compositions and process for fabricating an optical reflector constructed from biocompatible and bioresorbable silk fibroin proteins. For example, the silk retroreflectors may be built based on millimeter size microprism arrays to rotate the image plane of imaged cortical layers, thus enhancing the amount of photons that are detectable in the reflected direction when inserted in a sample to be analyzed, and ultimately increasing in contrast ratio in multiphoton microscopy. Such device can be used as a label-free, biocompatible, bioresorbable, implantable device for various applications ranging from medical imaging/diagnostics, drug/therapeutic delivery, to food chain safety and environmental monitoring.

20 Claims, 11 Drawing Sheets

(56) References Cited

U.S. PATENT DOCUMENTS

| | | | |
|---|---|---|---|
| 5,252,285 A | 10/1993 | Lock | |
| 5,427,096 A | 6/1995 | Bogusiewicz et al. | |
| 5,512,218 A | 4/1996 | Gresser et al. | |
| 6,134,045 A | 10/2000 | Jiang et al. | |
| 6,150,491 A | 11/2000 | Akkara | |
| 6,284,418 B1 | 9/2001 | Trantolo | |
| 6,481,857 B2 * | 11/2002 | Smith | 359/530 |
| 6,841,162 B2 * | 1/2005 | Philippe et al. | 424/401 |
| 6,924,503 B2 | 8/2005 | Cheng et al. | |
| 6,989,897 B2 | 1/2006 | Chan et al. | |
| 6,992,325 B2 | 1/2006 | Huang | |
| 7,057,023 B2 * | 6/2006 | Islam et al. | 530/412 |
| 7,223,609 B2 | 5/2007 | Anvar et al. | |
| 7,842,780 B2 * | 11/2010 | Kaplan et al. | 530/324 |
| 8,005,526 B2 | 8/2011 | Martin et al. | |
| 8,195,021 B2 * | 6/2012 | Kaplan et al. | 385/131 |
| 2001/0002417 A1 | 5/2001 | Akkara et al. | |
| 2001/0003043 A1 | 6/2001 | Metspalu et al. | |
| 2003/0203366 A1 | 10/2003 | Lim et al. | |
| 2003/0214057 A1 | 11/2003 | Huang | |
| 2004/0001299 A1 | 1/2004 | van Haaster et al. | |
| 2004/0029241 A1 | 2/2004 | Hahn et al. | |
| 2004/0081384 A1 | 4/2004 | Datesman et al. | |
| 2004/0229349 A1 | 11/2004 | Daridon | |
| 2005/0008675 A1 | 1/2005 | Bhatia et al. | |
| 2005/0151966 A1 | 7/2005 | Packirisamy et al. | |
| 2005/0194365 A1 | 9/2005 | Li | |
| 2005/0213868 A1 | 9/2005 | Cunningham | |
| 2005/0217990 A1 | 10/2005 | Sibbett et al. | |
| 2005/0276791 A1 | 12/2005 | Hansford et al. | |
| 2006/0042822 A1 | 3/2006 | Azeyanagi et al. | |
| 2006/0091571 A1 | 5/2006 | Akutsu et al. | |
| 2006/0134606 A1 | 6/2006 | Montagu | |
| 2006/0141617 A1 | 6/2006 | Desai et al. | |
| 2006/0177479 A1 | 8/2006 | Giachelli et al. | |
| 2006/0178655 A1 | 8/2006 | Santini et al. | |
| 2006/0226575 A1 | 10/2006 | Maghribi et al. | |
| 2006/0236436 A1 | 10/2006 | Li et al. | |
| 2006/0273279 A1 | 12/2006 | Kaplan et al. | |
| 2007/0007661 A1 | 1/2007 | Burgess et al. | |
| 2007/0009968 A1 | 1/2007 | Cunningham et al. | |
| 2007/0026064 A1 | 2/2007 | Yoder et al. | |
| 2007/0031607 A1 | 2/2007 | Dubson et al. | |
| 2007/0042505 A1 | 2/2007 | Israel et al. | |
| 2007/0058254 A1 | 3/2007 | Kim | |
| 2007/0073130 A1 | 3/2007 | Finch et al. | |
| 2007/0178240 A1 | 8/2007 | Yamazaki et al. | |
| 2007/0187862 A1 | 8/2007 | Kaplan et al. | |
| 2007/0212730 A1 | 9/2007 | Vepari et al. | |
| 2007/0233208 A1 | 10/2007 | Kurtz et al. | |
| 2008/0019925 A1 | 1/2008 | Begleiter | |
| 2008/0038236 A1 | 2/2008 | Gimble et al. | |
| 2008/0085272 A1 | 4/2008 | Kaplan et al. | |
| 2008/0152281 A1 | 6/2008 | Lundquist et al. | |
| 2008/0203431 A1 | 8/2008 | Garcia et al. | |
| 2008/0239755 A1 | 10/2008 | Parker et al. | |
| 2008/0280360 A1 | 11/2008 | Kaplan et al. | |
| 2008/0288037 A1 | 11/2008 | Neysmith et al. | |
| 2009/0028910 A1 | 1/2009 | DeSimone et al. | |
| 2009/0208555 A1 | 8/2009 | Kuttler et al. | |
| 2009/0232963 A1 | 9/2009 | Kaplan et al. | |
| 2010/0028451 A1 | 2/2010 | Kaplan et al. | |
| 2010/0046902 A1 * | 2/2010 | Kaplan et al. | 385/129 |
| 2010/0055438 A1 * | 3/2010 | Kaplan et al. | 428/221 |
| 2010/0063404 A1 | 3/2010 | Kaplan et al. | |
| 2010/0096763 A1 * | 4/2010 | Kaplan et al. | 264/1.1 |
| 2010/0120116 A1 | 5/2010 | Kaplan et al. | |
| 2011/0046652 A1 | 2/2011 | Rehnke et al. | |
| 2013/0243693 A1 * | 9/2013 | Omenetto et al. | 424/9.1 |

FOREIGN PATENT DOCUMENTS

| | | | | |
|---|---|---|---|---|
| EP | 1166987 A2 | 1/2002 | | |
| EP | 1467224 A1 | 10/2004 | | |
| JP | 60142259 A | 7/1985 | | |
| JP | 60155129 A | 8/1985 | | |
| JP | 01280242 A | 11/1989 | | |
| JP | 02086799 A | 3/1990 | | |
| JP | H03185183 A | 8/1991 | | |
| JP | 09230117 A | * 9/1997 | | G02B 5/08 |
| JP | 11042106 A | 2/1999 | | |
| JP | 2000096490 A | 4/2000 | | |
| JP | 2000143472 A | 5/2000 | | |
| JP | 2001147301 A | 5/2001 | | |
| JP | 2001280242 A | 10/2001 | | |
| JP | 2002287377 A | 10/2002 | | |
| JP | 2003195001 A | 7/2003 | | |
| JP | 2003195002 A | 7/2003 | | |
| JP | 2003322729 A | 11/2003 | | |
| JP | 2004162209 A | 6/2004 | | |
| JP | 2005530983 A | 10/2005 | | |
| JP | 2006241450 A | 9/2006 | | |
| KR | 20060027113 A | 3/2006 | | |
| KR | 20070060822 A | 6/2007 | | |
| KR | 20080069553 A | 7/2008 | | |
| WO | WO-9315244 A1 | 8/1993 | | |
| WO | WO-97/08315 A1 | 3/1997 | | |
| WO | WO-0031752 A2 | 6/2000 | | |
| WO | WO-0185637 A2 | 11/2001 | | |
| WO | WO-03038033 A2 | 5/2003 | | |
| WO | WO-04000915 A2 | 12/2003 | | |
| WO | WO-2004/062697 A2 | 7/2004 | | |
| WO | WO-2004092250 A1 | 10/2004 | | |
| WO | WO-2005012606 A2 | 2/2005 | | |
| WO | WO-2005019503 A2 | 3/2005 | | |
| WO | WO-2005/123114 A2 | 12/2005 | | |
| WO | WO-2006020507 A1 | 2/2006 | | |
| WO | WO-2006/076711 A2 | 7/2006 | | |
| WO | WO-2007/103442 A1 | 9/2007 | | |
| WO | WO-2008/106485 A2 | 9/2008 | | |
| WO | WO-2008/118133 A2 | 10/2008 | | |
| WO | WO-2008/127401 A2 | 10/2008 | | |
| WO | WO-2008118211 A2 | 10/2008 | | |
| WO | WO-2008127403 A2 | 10/2008 | | |
| WO | WO-2008127405 A2 | 10/2008 | | |
| WO | WO 2009/061823 A1 | 5/2009 | | |
| WO | WO-2009/140588 A1 | 11/2009 | | |
| WO | WO-2009/155397 A2 | 12/2009 | | |
| WO | WO-2010/040129 A2 | 4/2010 | | |
| WO | WO-2010/042798 A2 | 4/2010 | | |
| WO | WO-2010/057142 A2 | 5/2010 | | |
| WO | WO-2010059963 A2 | 5/2010 | | |
| WO | WO-2010126640 A2 | 11/2010 | | |
| WO | WO-2010/141133 A2 | 12/2010 | | |
| WO | WO-2011/006133 A2 | 1/2011 | | |
| WO | WO-2011/011347 A2 | 1/2011 | | |

OTHER PUBLICATIONS

International Search Report for PCT/US2010/042585, mailed May 25, 2011 (6 pages).

Written Opinion for PCT/US2010/042585, mailed May 25, 2011 (5 pages).

Bai, J. et al., Regenerated spider silk as a new biomaterial for MEMS, Biomed Microdevices, 8:317-323 (2006).

Chrisey, D.B. et al., Laser Deposition of Polymer and Biomaterial Films, Chem. Rev 103(2):553-576 (2003).

Fukuoka T. et al., Enzymatic Polymerization of Tyrosine Derivatives. Peroxidase- and Protease-Catalyzed Synthesis of Poly(tyrosine)s with Different Structures, Biomacromolecules 3(4):768-774 (2002).

International Search Report of PCT/US2007/083600, mailed Nov. 5, 2008, 5 pages.

International Search Report of PCT/US2007/083605, mailed Dec. 15, 2008, 6 pages.

International Search Report of PCT/US2007/083620, mailed Dec. 5, 2008, 4 pages.

International Search Report of PCT/US2007/083634, mailed Nov. 5, 2008, 5 pages.

International Search Report of PCT/US2007/083639, mailed Dec. 12, 2008, 5 pages.

International Search Report of PCT/US2007/083642, mailed Nov. 5, 2008, 5 pages.

(56) References Cited

OTHER PUBLICATIONS

International Search Report of PCT/US2007/083646, mailed Dec. 15, 2008, 6 pages.
International Search Report of PCT/US2008/082487, mailed Feb. 27, 2009, 3 pages.
International Search Report of PCT/US2009/047751, mailed Feb. 2, 2010, 3 pages.
International Search Report of PCT/US2010/022701, mailed Mar. 31, 2010, 2 pages.
International Search Report of PCT/US2010/024004, mailed Nov. 26, 2010, 5 pages.
International Search Report of PCT/US2010/047307, mailed Apr. 28, 2011, 3 pages.
International Search Report of PCT/US2010/050468, mailed Jan. 6, 2011, 3 pages.
International Search Report of PCT/US2011/028094, mailed Jul. 14, 2011, 4 pages.
International Search Report of PCT/US2011/032195, mailed Oct. 27, 2011, 3 pages.
International Search Report of PCT/US2011/041002, mailed Feb. 29, 2012, 4 pages.
IPRP of PCT/US2007/083600, mailed May 5, 2009, 6 pages.
IPRP of PCT/US2007/083605, mailed May 5, 2009, 10 pages.
IPRP of PCT/US2007/083620, mailed May 5, 2009, 6 pages.
IPRP of PCT/US2007/083634, mailed May 5, 2009, 6 pages.
IPRP of PCT/US2007/083639, mailed May 5, 2009, 6 pages.
IPRP of PCT/US2007/083642, mailed May 5, 2009, 6 pages.
IPRP of PCT/US2007/083646, mailed May 5, 2009, 10 pages.
IPRP of PCT/US2008/082487, mailed May 11, 2010, 10 pages.
IPRP of PCT/US2009/047751, mailed Dec. 18, 2010, 5 pages.
IPRP of PCT/US2010/022701, mailed Aug. 2, 2011, 5 pages.
IPRP of PCT/US2010/024004, mailed Aug. 16, 2011, 6 pages.
IPRP of PCT/US2010/042585, mailed Jan. 24, 2012, 6 pages.
IPRP of PCT/US2010/047307, mailed Mar. 6, 2012, 5 pages.
Jiang, W. et al, Silicon and Polymer Nanophotonic Devices Based on Photonic Crystals, Proceedings of the International Society of Optical Engineering, 6124(1):612410-1(2006).
Jin, I.J. et al., Water-Stable Silk Films with Reduced Beta-Sheet Content, Adv. Funct. Mater., 15:1241-1247 (2005).
Kouba et al., Fabrication of Nanoimprint Stamps for Photonic Crystals, Journal of Physics: Conference Series, 34(1):897-903 (2006).
Lawrence, B.D. et al., Bioactive silk protein biomaterial systems for optical devices, Biomacromolecules, 9:1214-1220 (2008).
Min, B.M. et al., Regenerated Silk Fibroin Nanofibers: Water Vapor-Induced Structural Changes and Their Effects on the Behavior of Normal Human Cells, Macromol. Biosci., 6(4):285-292 (2006).
Minoura, N. et al., Attachment and Growth of Cultured Fibroblast Cells on Silk Protein Matrices, J. Biomed. Mater. Res. 29(10):1215-1221 (1995).
Notification of Transmittal of International Search Report and the Written Opinion of PCT/US2011/032195, mailed Oct. 27, 2011, 2 pages.
Ramanujam, P.S., Optical Fabrication of Nano-Structured Biopolymer Surfaces, Opt. Mater. 27:1175-1177 (2005).
Tu, D. et al., A ZEP520-LOR Bilayer Resist Lift-Off Process by E-Beam Lithography for Nanometer Pattern Transfer, Proceedings of the 7th IEEE Conference on Nanotechnology, 624-627 (2007).
Verma, M.K. et al., Embedded Template-Assisted Fabrication of Complex Microchannels in PDMS and Design of a Microfluidic Adhesive, Langmuir, 22(24)10291-10295 (2006).
Wang, L. et al., Fabrication of Polymer Photonic Crystal Superprism Structures Using Polydimethylsiloxane Soft Molds Journal of Applied Physics, 101(11):114316/1-6 (2007).
Written Opinion of PCT/US2007/083600, mailed Nov. 5, 2008, 5 pages.
Written Opinion of PCT/US2007/083605, mailed Dec. 15, 2008, 9 pages.
Written Opinion of PCT/US2007/083620, mailed Dec. 5, 2008, 5 pages.
Written Opinion of PCT/US2007/083634, mailed Nov. 5, 2008, 5 pages.
Written Opinion of PCT/US2007/083639, mailed Dec. 12, 2008, 5 pages.
Written Opinion of PCT/US2007/083642, mailed Nov. 5, 2008, 5 pages.
Written Opinion of PCT/US2007/083646, mailed Dec. 15, 2008, 9 pages.
Written Opinion of PCT/US2008/082487, mailed Feb. 27, 2009, 9 pages.
Written Opinion of PCT/US2009/047751, mailed Feb. 2, 2010, 4 pages.
Written Opinion of PCT/US2010/022701, mailed Mar. 31, 2010, 4 pages.
Written Opinion of PCT/US2010/024004, mailed Nov. 23, 2010, 5 pages.
Written Opinion of PCT/US2010/047307, mailed on Apr. 28, 2011, 4 pages.
Written Opinion of PCT/US2011/032195, mailed Oct. 27, 2011, 5 pages.
Xu, P. and Kaplan, D.L., Horseradish peroxidase catalyzed polymerization of tyrosine derivatives for nanoscale surface patterning, Journal of Macromolecular Science, Part A: Pure and Applied Chemistry, 41(12):1437-1445 (2004).
Yang, L.J. et al., Fabrication of SU-8 embedded microchannels with circular cross-section, International Journal of Machine Tools & Manufacturing, 44:1109-1114 (2004).
Altman, G. et al., Silk-based biomaterials, Biomaterials, 24(3):401-416 (2003).
Amsden, J. et al., Rapid Nanoimprinting of Silk Fibroin Films for Biophotonic Applications, Advanced Materials, 22:1746-1749 (2010).
Chia, T. and Levene, M., Microprisms for in vivo multilayer cortical imaging, Journal of Neurophysiology, 102(2):1310-1314 (2009).
Deutsch, Thomas F., Lasers and Optics in Health Care, Proceedings of the IEEE, 85(11):1797-1816 (1997).
Dong, L. et al., Adaptive liquid microlenses activated by stimuli-responsive hydrogels, Nature, 442(7102):551-554 (2006).
Hagen, J.A. et al., Enhanced emission efficiency in organic light-emitting diodes using deoxyribonucleic acid complex as an electron blocking layer, Applied Physics Letters, 88:171109-1-171109-3 (2006).
Howard, D. et al., Immunoselection and adenoviral genetic modulation of human osteoprogenitors: in vivo bone formation on PLA scaffold, Biochemical and Biophysical Research Communications, 299(2):208-215 (2002).
Jiang, C. et al., Mechanical Properties of Robust Ultrathin Silk Fibroin Films, Advanced Functional Materials, 17: 2229-2237 (2007).
Lu, Q. et al., Water-insoluble silk films with silk I structure, Acta Biomaterialia, 6(4):1380-1387 (2010).
Lucas, F. et al., The silk fibroins, Advances in Protein Chemistry, 107-242 (1958).
Lundvall, A. and Nikolajeff, F., High performing micromachined retroreflector, Optics Express, 11(20):2459-2473 (2003).
Matcher, S. J. et al., In vivo measurements of the wavelength dependence of tissue-scattering coefficients between 760 and 900 nm measured with time-resolved spectroscopy, Applied Optics, 36(1):386-396 (1997).
Murphy, A. et al., Modification of silk fibroin using diazonium coupling chemistry and the effects on hMSC proliferation and differentiation, Biomaterials, 29(19):2829-2838 (2008).
Omenetto, F. and Kaplan, D., A new route for silk, Nature Photonics, 2:641-643 (2008).
Partridge, K. et al., Adenoviral BMP-2 gene transfer in mesenchymal stem cells: in vitro and in vivo bone formation on biodegradable polymer scaffolds, Biochemical and Biophysical Research Communications, 292(1):144-152 (2002).
Perry, H. et al., Nano- and Micropatterning of Optically Transparent, Mechanically Robust, Biocompatible Silk Fibroin Films, Advanced Materials, 20:3070-3072 (2008).

(56) References Cited

OTHER PUBLICATIONS

Santin, M. et al., In vitro evaluation of the inflammatory potential of the silk fibroin, Journal of Biomedical Materials Research, 46(3):382-389 (1999).

Sofia, S. et al., Functionalized silk-based biomaterials for bone formation, Journal of Biomedical Materials Research, 54:139-148 (2001).

Steckl, Andrew J., DNA—a new material for phonics?, Nature Photonics, 3:3-5 (2007).

Stone, K. et al., Regeneration of meniscal cartilage with use of a collagen scaffold. Analysis of preliminary data, Journal of Bone and Joint Surgery, 79(12):1770-1777 (1997).

Szybala, C. et al., Antiepileptic effects of silk-polymer based adenosine release in kindled rats, Experimental Neurology, 219(1):126-135 (2009).

Wang, L. et al., MCML—Monte Carlo modeling of light transport in multi-layered tissues, Computer Methods & Programs Biomedicine, 47:131-146 (1995).

Wang, X. et al., Controlled release from multilayer silk biomaterial coatings to modulate vascular cell responses, Biomaterials, 29:894-903 (2008).

Wilz, A. et al., Silk polymer-based adenosine release: Therapeutic potential for epilepsy, Biomaterials, 29:3609-3616 (2008).

Xia, Y. and Whitesides, G. Soft Lithography, Angewandte Chemie International Edition, 37:550-575 (1998).

Zaccanti, G. et al., Analytic relationships for the statistical moments of scattering point coordinates for photon migration in a scattering medium, Pure and Applied Optics, 3:897-905 (1994).

Zonios, G. and Dimou, A., Light scattering spectroscopy of human skin in vivo, Optics Express, 17(3):1256-1267 (2009).

\* cited by examiner

ALL-PROTEIN IMPLANTABLE, RESORBABLE REFLECTORS

CROSS REFERENCE TO RELATED APPLICATIONS

This application is a 35 U.S.C. §371 National Stage of International Application No. PCT/US2010/042585, entitled "All-Protein Implantable, Resorbable Reflectors" and filed on Jul. 20, 2010 and claims the benefit of priority of U.S. Provisional Application Ser. No. 61/226,801, entitled "All-Protein Implantable, Resorbable Reflectors" and filed Jul. 20, 2009, the contents of which are incorporated herein by reference in their entirety.

GOVERNMENT SUPPORT

This invention was made with government support under EB002520 awarded by the National Institutes of Health, W911NF-07-1-0618 awarded by the Army Research Office, and FA9550-07-1-0079 awarded by the Air Force Office of Scientific Research. The government has certain rights in the invention.

FIELD OF THE INVENTION

This invention relates to the field of biophotonic and biomedical devices. More specifically, the embodiments of the invention provide for silk fibroins as novel biocompatible, bioresorbable, and implantable reflective components or devices for various applications ranging from medical imaging/diagnostics, drug/therapeutic delivery, bio sensing, to food chain safety and environmental monitoring.

BACKGROUND OF THE INVENTION

Medical imaging is extending human vision into the nature of disease and tissue function, allowing a novel and more powerful generation of diagnosis and intervention. Deutsch, 85 Proceedings of the IEEE 1797-816 (1997). Optical methods have been explored to develop novel medical imaging applications in areas such as detection of disease, assessment of tissue function, and therapeutic interventions. For example, confocal and non-linear microscopy, optical coherence tomography, and diffuse optical tomography are biomedical optics technique capable of investigating biological tissues over depths in the order of ~0.1 mm, ~1 mm, and ~1 cm, respectively.

In spite of this pivotal role, imaging techniques still present challenges, including the optical transmission limitations of natural tissue imposed by scattering and absorption that curb the image resolution and the depth of observation. Matcher et al., 36 Appl. Opt. 386-96 (1997); Zonios & Dimou, 17 Opt. Express 1256-67 (2009). The imaging techniques are also limited by the amount and type of information that can be relayed by the optical system. These problems often require resorting to methods for enhancing image quality through, for example, introducing exogenous contrast agents or radioactive markers that can be invasive or toxic or resorting to probes for imaging such as those afforded by endoscopy. There is a need to overcome these limitations and expand the utility of optical devices that ultimately affect an individual's anamnesis. More specifically, there remains a need in the art of biomedical device field to develop biocompatible, biodegradable and/or bioresorbable photonic components and devices that need no retrieval after incorporation in the body, and at the same time, provide high-quality optical properties and sensitivities.

SUMMARY OF THE INVENTION

One aspect of the invention relates to compositions and methods for fabricating an optical reflector constructed from biocompatible and bioresorbable silk fibroin proteins. The silk optical components were used and characterized by in vitro and in vivo optical measurements, which demonstrated signal enhancements through different scattering/absorption medium (e.g., layers of tissues), exerted no adverse biological effects, and exhibited slow degradability and the ability to integrate into native tissue in vivo. Such silk reflectors can be used as a novel class of biocompatible and bioabsorbable optical devices in medical imaging and diagnosis field suited for optical and photonic component fabrication and, at the same time, can be introduced inside the human body without the need for retrieval.

One aspect of the invention relates to a process for fabricating a silk reflector, comprising the step of forming a reflective element or an array of reflective elements onto the surface of a silk film.

Another aspect of the invention relates to a silk reflector comprising one or more layers of silk film, where a reflective element or an array of reflective elements is formed onto the surface of the silk film or each layer of the silk film.

The reflective element or the array of reflective elements may be formed on the surface of a silk film through replicating from a master pattern having the reflective element or the array of reflective elements. Alternatively, the reflective element or the array of reflective elements may be formed on the surface of a silk film through dispersing reflective particles in or on the surface the silk film. For example, the reflective particles may be metal nanoparticles such as gold or silver nanoparticles, or combinations thereof.

Another aspect of the invention relates to an implantable silk reflector having optical utility for in vivo operation, comprising at least one layer of silk film having a reflective element or an array of reflective elements formed onto the surface of the silk layer. The resulting silk reflector is biocompatible and bioresorbable. The reflective element may be a microprism or array of microprisms.

BRIEF DESCRIPTION OF THE DRAWINGS

FIGS. 1B and 1D show the different magnifications of the individual prisms, and FIG. 1C shows the side image of the associated film illustrating the section of the individual prisms.

FIGS. 5A, 5C and 5E are collected images on the CCD camera and FIGS. 5B, 5D and 5F show corresponding intensity profiles for the collected images of FIGS. 5A, 5C and 5E, respectively. FIGS. 5A and 5B show the comparison of the images (FIG. 5A) and corresponding intensity profiles (FIG. 5B) for reflectivity of the bare master (the left image and intensity profile) and bare silk replica (the right image and intensity profile); FIGS. 5C and 5D show the comparison of the images (FIG. 5C) and corresponding intensity profiles (FIG. 5D) for reflectivity of the master (the left image and intensity profile) and silk replica (the right image and intensity profile) under red light illumination; and FIGS. 5E and 5F show the comparison of the images (FIG. 5E) and corresponding intensity profiles (FIG. 5F) of a retroreflective film (the left image and intensity profile) and a clear silk film (the right image and intensity profile) under a 2 cm thick layer of gelatin.

FIG. 7A is a schematic showing that the silk reflector was exposed to isotropic illumination from a white light source, and the reflection from the silk reflector was collected at a distance of 1.5 meters with a digital CCD camera. The inset images of FIG. 7B show the collected CCD images of the silk reflector (the left image) and a flat silk substrate (the right image) under 3.5 cm of gelatin; and the graph of FIG. 7B shows corresponding intensity profiles extracted from the image for the silk reflector (1) and a flat silk substrate (2), respectively. The inset image of FIG. 7C shows the collected image from the CCD when the silk reflector was immersed under 6.5 cm of scattering solution composed of talcum and water. The silk reflector was attached to the bottom of a dark container and then covered with the solution. The graph of FIG. 7C shows corresponding intensity profile extracted from cross sections of the image including the reflector (1) and the background (2).

FIGS. 8A-8B show the results from in vitro experiments with incoherent illumination and detection through a fiber probe of the backscattered spectrum from deep tissue layers. FIG. 8A is a schematic illustrating the in vitro experiment setup, where a silk reflector is placed underneath a spectrally responsive element to capture scattered photons in the forward direction and enhanced the backscattered signal. FIG. 8B shows the spectral response when the spectrally responsive element is a pigmented cellulose layer and FIG. 8C shows the spectral response when a silk reflector is placed underneath a multilayered spectral filter.

FIG. 9A is a schematic illustrating the in vitro experiment setup, where a silk reflector is placed underneath a spectrally responsive element to capture scattered photons in the forward direction and enhanced the backscattered signal. FIG. 9B shows the intensity profiles comparing the signal detected from (1) the spectral element covered by one layer of fat, (2) the spectral element covered by two fat layers and (3) the spectral element covered by two fat layers, with the silk reflector placed underneath the spectral element. The response was significantly higher when the silk reflector was present. FIG. 9C shows the results from the similar experiment replacing the layers of fat with layers of muscle tissue: (1) the response due to the spectral element covered with two layers of muscle tissue, and (2) the response due to the spectral element covered with two layers of muscle tissue, with the silk reflector placed underneath the spectral element.

FIG. 11A is a picture showing a subcutaneous implantation of silk reflectors in the dorsal region of a mouse. The implant was 1 cm×1 cm and is visible. FIG. 11B shows the result of the same implant after 20 days indicating no sign of infection and an increase of signal from probing the area with the implant in comparison to an implant-free portion of the mouse. FIG. 11C shows an increased backscattered signal right after implantation of the silk reflectors (a) comparing to a control signal taken from an implantless site (b). FIG. 11D illustrates the pathology section from H & E staining. The silk film with the microprisms visible (2) is in contact with subcutaneous tissue (3 & 4), indicating a thickening of the hypodermis directly under the implant (3) when compared to deeper hypodermis (4), no influx of inflammatory cells or indication of a significant biological response to the implant. The subcutaneous fat layer (5) is unaffected.

DETAILED DESCRIPTION

Figure 1:
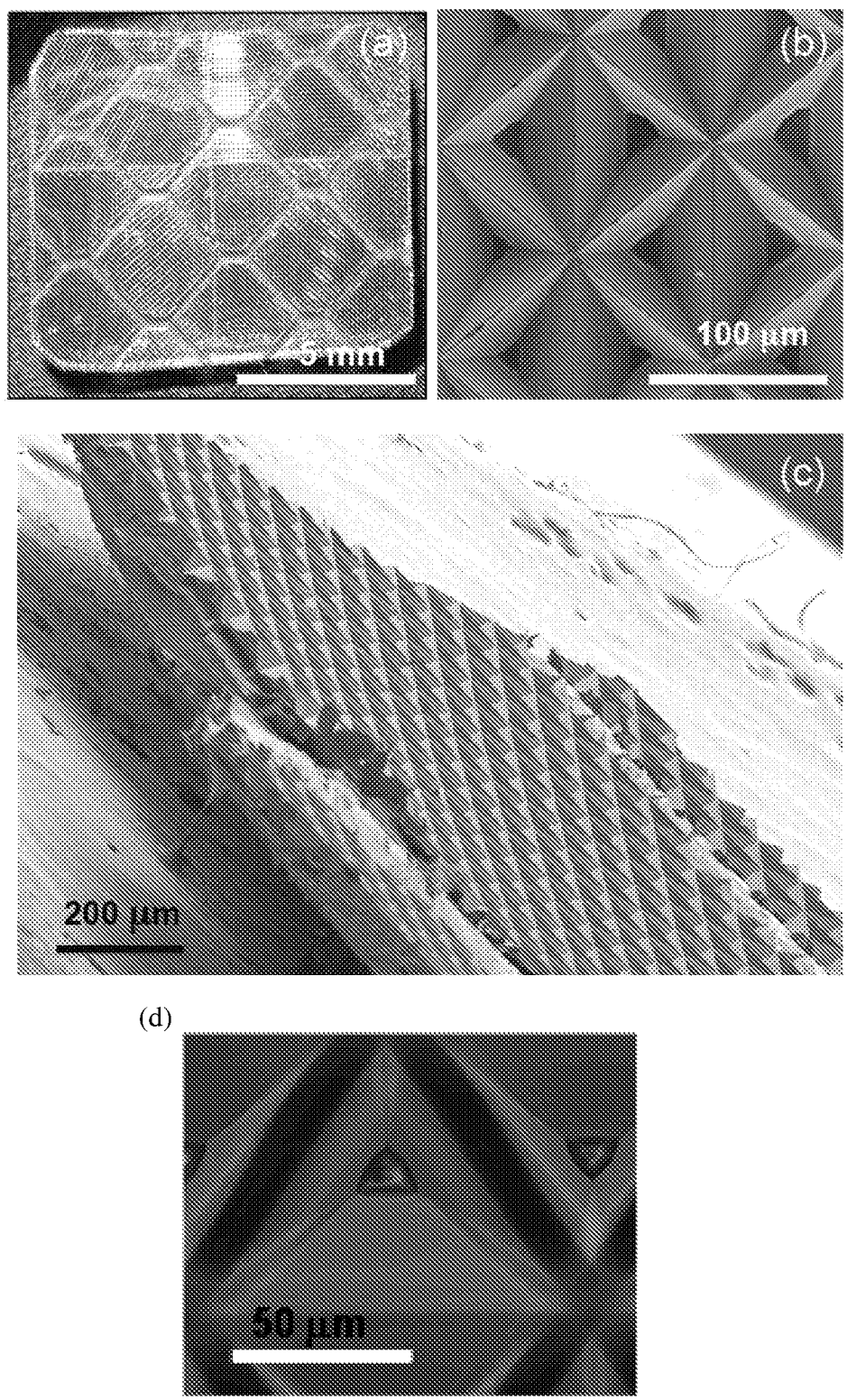
FIG. 1A is a picture showing a free standing 1×1.5 cm silk reflector film.
FIGS. 1B-1D are scanning electron microscope images showing the magnified images of the silk reflector.

One aspect of the invention relates to compositions and methods for fabricating an optical reflector constructed by biocompatible and bioresorbable silk fibroin proteins, thus providing an implantable component/device of optical utility, and capable of being incorporated in vivo as a resorbable optical device/component. For example, the silk retroreflectors may utilize millimeter size microprism arrays to rotate the image plane of imaged cortical layers, thus enhancing the amount of photons that are detectable in the reflected direction when inserted in a sample to be analyzed, and ultimately increasing the contrast ratio in multiphoton microscopy. Developing such material platforms addresses the need in medical imaging and diagnosis field for materials that are suited for optical and photonic component fabrication and at the same time can be introduced inside the human body without the need for retrieval.

The above material approach can provide a paradigm shift from today's implantable optical devices. For example, optics and photonics devices/components can be manufactured with materials, such as silk fibroins, that are simultaneously biocompatible, implantable and bioresorbable, allowing the devices to be fully integrated into regenerated native tissues over time once their diagnostic utility is exhausted, thereby eliminating the need for retrieval. This can extend the utility of in vivo screening modalities where optical responses are generated from the diagnostic site of interest, ultimately transforming native tissue into an optical interface. On the other hand, optics and photonic devices/components prepared from such materials introduced directly inside the human body can also allow the detection of enhanced endogenous optical responses or selected spectral portions of a diagnostic interest.

The use of biopolymers is increasingly prevalent in optoelectronic and photonic devices. Steckl et al., 1 Nat. Photonics 3 (2007); Hagen et al., 88 Applied Phys. Lett. 171109 (2006); Dong et al., 442 Nature 551 (2006). Polymers such as polylactic acids (Howard et al., 299 Biochem. Biophys. Res. Commun. 208 (2002); Partridge et al., 292 Biochem. Biophys. Res. Commun. 144 (2002)) and collagens (Stone et al., 79 J. Bone Joint Surg. Am. 1770 (1997)) have been used as implantable, resorbable biomaterial matrices. The material platforms in the above approach require the polymer materials to provide optical features and performance comparable to common optical substrates, such as glass, plastics or (inorganic) polymers. Purified silk possesses a convenient confluence of such traits.

Silk fibroin is a particularly appealing biopolymer candidate for forming such devices because of its optical properties (Lawrence et al., 9 Biomacromolecules 1214 (2008)), mechanical properties (Altman et al., 24 Biomat. 401 (2003); Jiang et al., 17 Adv. Funct. Mater. 2229 (2007)), all aqueous processing (Sofia et al., 54 J. Biomed. Mater. Res. 139 (2001); Perry et al., 20 Adv. Mater. 3070-72 (2008)), relatively easy functionalization (Murphy et al., 29 Biomat. 2829-38 (2008)), and biocompatibility (Santin et al., 46 J. Biomed. Mater. Res. 382-9 (1999)). For example, silk fibroin can be processed into thin, mechanically robust films with excellent surface quality and optical transparency.

Silk has been used in human implants as a Food and Drug Administration approved tissue engineering scaffold. Altman et al., 24 Biomaterials: 401 (2003). Reprocessed silk has been recently shown to be suitable as a material platform to manufacture sophisticated optical components with features on the micro- and nanoscale. Amsden et al., 22 Adv. Mater. 1-4 (2010); Lawrence et al., 9 Biomacromolecules 1214 (2008); Omenetto & Kaplan, 2 Nat. Photonics 641 (2008); Perry et al., 20 Adv. Mater. 3070 (2008). Optical components made from the free-standing reprocessed silk are refractive or diffractive, and comprise elements ranging from microlens arrays, white light holograms, to diffraction gratings and planar photonic crystals with minimum feature sizes of less than 20 nanometers. These components, which are entirely constituted by silk, possess properties needed to provide mechanically stable, high-quality optical elements that are fully degradable, biocompatible and implantable. Omenetto & Kaplan, 2008.

As used herein, the term "silk fibroin" includes silkworm fibroin and insect or spider silk protein. See e.g., Lucas et al., 13 Adv. Protein Chem. 107 (1958). Any type of silk fibroin may be used according to the present invention. Silk fibroin produced by silkworms, such as *Bombyx mori*, is the most common and represents an earth-friendly, renewable resource. For instance, silk fibroin used in a silk optical film may be attained by extracting sericin from the cocoons of *B. mori*. Organic silkworm cocoons are also commercially available. There are many different silks, however, including spider silk (e.g., obtained from *Nephila clavipes*), transgenic silks, genetically engineered silks, such as silks from bacteria, yeast, mammalian cells, transgenic animals, or transgenic plants (see, e.g., WO 97/08315; U.S. Pat. No. 5,245,012), and variants thereof, that may be used.

An aqueous silk fibroin solution may be prepared using techniques known in the art. Suitable processes for preparing silk fibroin solution are disclosed, for example, in U.S. patent application Ser. No. 11/247,358; WO/2005/012606; and WO/2008/127401. The silk aqueous solution can then be processed into silk matrix such as silk films, conformal coatings or layers, or 3-dimensional scaffolds, or electrospun fibers for further processing into the silk reflectors. A microfiltration step may be used herein. For example, the prepared silk fibroin solution may be processed further by centrifugation and syringe based micro-filtration before further processing into silk matrix. This process enables the production of silk fibroin solution of excellent optical quality and stability. The micro-filtration step is often desirable for the generation of high-quality optical films with minimized scattering.

Other biocompatible and biodegradable polymers may be blended in the silk film. For example, additional biopolymers, such as chitosan, exhibit desirable mechanical properties, can be processed in water, blended with silk fibroin, and form generally clear films for optical applications. Other biopolymers, such as chitosan, collagen, gelatin, agarose, chitin, polyhydroxyalkanoates, pullan, starch (amylose amylopectin), cellulose, alginate, fibronectin, keratin, hyaluronic acid, pectin, polyaspartic acid, polylysin, pectin, dextrans, and related biopolymers, or a combination thereof, may be utilized in specific applications, and synthetic biodegradable polymers such as polyethylene oxide, polyethylene glycol, polylactic acid, polyglycolic acid, polycaprolactone, polyorthoester, polycaprolactone, polyfumarate, polyanhydrides, and related copolymers may also be selectively used. The polymer selected herein to be blended into the silk films should not negatively impact the optical quality or stability of silk films.

The silk fibroin film may be prepared by depositing an aqueous silk fibroin-containing solution on a support substrate and allowing the silk fibroin solution to dry into a film. In this regard, the substrate coated with silk fibroin-based solution may be exposed in air for a period of time, such as 12 hours. Depositing the silk fibroin solution can be performed by, e.g., using a spin coating method, where the silk fibroin solution is spin coated onto the substrate to allow the fabrication of thin membranes of non-uniform in height; or simply by pouring silk fibroin solution over the top of the substrate. The properties of the silk fibroin film, such as thickness and content of other components, as well as optical features, may be altered based on the concentration and/or the volume of the silk fibroin solution applied to the substrate, and the techniques used for processing the silk fibroin solution into silk film. For instance, the thickness of the silk film may be controlled by changing the concentration of the silk fibroin in the solution, or by using desired volumes of silk fibroin solution, resulting silk fibroin film with a thickness ranging from approximately 2 nm to 1 mm thick. In one embodiment, one can spin coat the silk fibroin onto a substrate to create films having thickness from about 2 nm to about 100 µm using various concentrations of silk fibroin and spinning speeds. The silk fibroin films formed herein have excellent surface quality and optical transparency.

In one aspect of the invention, provided is a process for fabricating a silk reflector, comprising the step of forming a reflective element or an array of reflective elements onto the surface of a silk film. Another aspect of the invention also provides a silk reflector comprising one or more layers of silk film, where a reflective element or an array of reflective elements is formed onto the surface of the silk film or each layer of the silk film.

In some embodiments, the reflective element or the array of reflective elements may be formed on the surface of a silk film through replicating from a master pattern having the reflective element or the array of reflective elements.

Alternatively, the reflective element or the array of reflective elements may be formed on the surface of a silk film through dispersing reflective particles in or on the surface the silk film. For example, the reflective particles may be metal nanoparticles such as gold or silver nanoparticles, or combinations thereof.

The term "master pattern" as used herein refers to a mold or a template possessing the desired pattern to be replicated on the surface of the silk film. The master pattern may be a milli- micro- or nanopatterned surface and/or may be an optical device such as a lens, microlens, microlens array, prisms, microprisms array, pattern generator, and the like, depending on the reflective features desired for the silk reflectors or depending on the reflective features desired in the optical device comprising the silk reflectors.

The reflective elements replicated from the master pattern may be a single reflective element or reflective elements in a 1D, 2D or 3D array. The reflective elements may be mirrors and retroreflectors with various shapes and geometries, including but not limited to flat mirrors, diamond-cut reflectors, retroreflectors with geometries such as a corner-cube, hemispherical geometry, "cat's-eye" geometry or the mirror-backed lens (see, e.g., Lundvall et al., 11 Optics Express, 2459 (2003)), retro-reflecting cavities containing plurality of orthogonal intersecting planes, such as the corners of square, rectangular, or cubical cavities.

The term "retroreflective" as used herein refers to the attribute of reflecting an obliquely incident light ray in a direction antiparallel to its incident direction, or nearly so, such that it returns to the light source or the immediate vicinity thereof. Retroreflectors can, over a broad angle, return light toward its source. Hence they are highly detectable by using simple illumination and detection with or without spectral filters. Retroreflectors may be used in a wide range of applications from retroreflective paints to enhance reflective brightness on signs or markers for macroscale retroreflectors, to biological recognition elements in medical imaging, bioassays or biosensors for microscale retroreflectors.

The silk reflective elements can be manufactured by techniques known to one skilled in the art. In one embodiment, micromolding techniques akin to soft lithography (Perry et al., 20 Adv. Mater. 3070 (2008); Xia & Whitesides, 37 Angew. Chem. Int. Ed. 550 (1998)) was used to prepare the silk implantable optical component by replicating a reflective microprism array master mask. See also WO 2009/061823. For example, silk fibroin films can be patterned on the micro- and nano-scale using a soft lithography casting technique in which silk fibroin solution is cast on a pattern and dried. See Perry et al., 2008. The resulting device was a 100 µm thick free-standing silk reflector film with dimensions ranging from a few to a few tens of square centimeters, as shown in FIG. 1.

In other embodiments, room temperature nanoimprinting technique may also be used to prepare the silk reflective components with fine features, such as those features having a minimum dimension of about 20 nm or less. See PCT/US2010/024004. Using the room-temperature nanoimprinting technique, the biological activity of some facile bioactive agents that are particularly sensitive to temperature can be preserved, further enabling facile production of bioactive nanoscale devices based on the silk implantable optical devices/components.

In some embodiments, the silk reflector is used as retroreflector.

In some embodiments, the silk reflector presents enhanced reflectivity and sensitivity when illuminated with a broadband light. The illumination can be simple white light without spectral filtering.

In some embodiments, the silk reflector presents enhanced reflectivity and sensitivity at specific wavelengths, for example the illumination may be filtered to a specific wavelength such as a specific wavelength at a visible spectrum. In some embodiments, the spectral element applied above the silk reflector can be multilayers of spectral filters.

Some embodiments of the invention are based on generating a free-standing reflector film constituted by a two dimensional (2-D) silk-microprism array. These silk-microprism arrays were integrated with scattering media and biological tissue, and both in vivo and in vitro behaviors were studied.

The passive silk implantable optical component/device can be utilized in many aspects. For instance, it can be used to increase the amount of light that returns to a detector when a biological specimen is probed optically.

At least one active agent may be added into silk films or multiple silk layers. Active agent may be added into the silk fibroin solution before or during the processing of silk fibroin solution into silk film.

The active agent can represent any material capable of being embedded in the silk film. For example, the agent may be a therapeutic agent, or a biological material, such as cells (including stem cells), proteins, peptides, nucleic acids (e.g., DNA, RNA, siRNA), nucleic acid analogs, nucleotides, oligonucleotides, peptide nucleic acids (PNA), aptamers, antibodies or fragments or portions thereof (e.g., paratopes or complementarity-determining regions), antigens or epitopes, hormones, hormone antagonists, growth factors or recombinant growth factors and fragments and variants thereof, cell attachment mediators (such as RGD), cytokines, cytotoxins, enzymes, small molecules, drugs, dyes, amino acids, vitamins, antioxidants, antibiotics or antimicrobial compounds, anti-inflammation agents, antifungals, viruses, antivirals, toxins, prodrugs, chemotherapeutic agents, or combinations thereof. See, e.g., PCT/US09/44117; U.S. Patent Application Ser. No. 61/224,618). The agent may also be a combination of any of the above-mentioned agents. Encapsulating either a therapeutic agent or biological material, or the combination of them, is desirous because the encapsulated product can be used for numerous biomedical purposes.

In some embodiments, the active agent may also be an organism such as a fungus, plant, animal, bacterium, or a virus (including bacteriophage). Moreover, the active agent may include neurotransmitters, hormones, intracellular signal transduction agents, pharmaceutically active agents, toxic agents, agricultural chemicals, chemical toxins, biological toxins, microbes, and animal cells such as neurons, liver cells, and immune system cells. The active agents may also include therapeutic compounds, such as pharmacological materials, vitamins, sedatives, hypnotics, prostaglandins and radiopharmaceuticals.

Exemplary cells suitable for use herein may include, but are not limited to, progenitor cells or stem cells, smooth muscle cells, skeletal muscle cells, cardiac muscle cells, epithelial cells, endothelial cells, urothelial cells, fibroblasts, myoblasts, oscular cells, chondrocytes, chondroblasts, osteoblasts, osteoclasts, keratinocytes, kidney tubular cells, kidney basement membrane cells, integumentary cells, bone marrow cells, hepatocytes, bile duct cells, pancreatic islet cells, thyroid, parathyroid, adrenal, hypothalamic, pituitary, ovarian, testicular, salivary gland cells, adipocytes, and precursor cells. The active agents can also be the combinations of any of the cells listed above. See also WO 2008/106485; PCT/US2009/059547; WO 2007/103442.

Exemplary antibodies that may be incorporated in silk fibroin include, but are not limited to, abciximab, adalimumab, alemtuzumab, basiliximab, bevacizumab, cetuximab, certolizumab pegol, daclizumab, eculizumab, efalizumab, gemtuzumab, ibritumomab tiuxetan, infliximab, muromonab-CD3, natalizumab, ofatumumab omalizumab, palivizumab, panitumumab, ranibizumab, rituximab, tositumomab, trastuzumab, altumomab pentetate, arcitumomab, atlizumab, bectumomab, belimumab, besilesomab, biciromab, canakinumab, capromab pendetide, catumaxomab, denosumab, edrecolomab, efungumab, ertumaxomab, etaracizumab, fanolesomab, fontolizumab, gemtuzumab ozogamicin, golimumab, igovomab, imciromab, labetuzumab, mepolizumab, motavizumab, nimotuzumab, nofetumomab merpentan, oregovomab, pemtumomab, pertuzumab, rovelizumab, ruplizumab, sulesomab, tacatuzumab tetraxetan, tefibazumab, tocilizumab, ustekinumab, visilizumab, votumumab, zalutumumab, and zanolimumab. The active agents can also be the combinations of any of the antibodies listed above.

Exemplary antibiotic agents include, but are not limited to, actinomycin; aminoglycosides (e.g., neomycin, gentamicin, tobramycin); β-lactamase inhibitors (e.g., clavulanic acid, sulbactam); glycopeptides (e.g., vancomycin, teicoplanin, polymixin); ansamycins; bacitracin; carbacephem; carbapenems; cephalosporins (e.g., cefazolin, cefaclor, cefditoren, ceftobiprole, cefuroxime, cefotaxime, cefipeme, cefadroxil, cefoxitin, cefprozil, cefdinir); gramicidin; isoniazid; linezolid; macrolides (e.g., erythromycin, clarithromycin, azithromycin); mupirocin; penicillins (e.g., amoxicillin, ampicillin, cloxacillin, dicloxacillin, flucloxacillin, oxacillin, piperacillin); oxolinic acid; polypeptides (e.g., bacitracin, polymyxin B); quinolones (e.g., ciprofloxacin, nalidixic acid, enoxacin, gatifloxacin, levaquin, ofloxacin, etc.); sulfonamides (e.g., sulfasalazine, trimethoprim, trimethoprim-sulfamethoxazole (co-trimoxazole), sulfadiazine); tetracyclines (e.g., doxycyline, minocycline, tetracycline, etc.); monobactams such as aztreonam; chloramphenicol; lincomycin; clindamycin; ethambutol; mupirocin; metronidazole; pefloxacin; pyrazinamide; thiamphenicol; rifampicin; thiamphenicl; dapsone; clofazimine; quinupristin; metronidazole; linezolid; isoniazid; piracil; novobiocin; trimethoprim; fosfomycin; fusidic acid; or other topical antibiotics. Optionally, the antibiotic agents may also be antimicrobial peptides such as defensins, magainin and nisin; or lytic bacteriophage. The antibiotic agents can also be the combinations of any of the agents listed above. See also PCT/US2010/026190.

Exemplary enzymes suitable for use herein include, but are not limited to, peroxidase, lipase, amylose, organophosphate dehydrogenase, ligases, restriction endonucleases, ribonucleases, DNA polymerases, glucose oxidase, laccase, and the like. Interactions between components may also be used to functionalize silk fibroin through, for example, specific interaction between avidin and biotin. The active agents can also be the combinations of any of the enzymes listed above. See U.S. Patent Application Ser. No. 61/226,801.

When introducing therapeutic agents or biological materials into silk films, other materials known in the art may also be added with the active agent. For instance, it may be desirable to add materials to promote the growth of the agent (for biological materials), promote the functionality of the agent after it is released from the silk film, or increase the agent's ability to survive or retain its efficacy during the period it is embedded in the silk. Materials known to promote cell growth include cell growth media, such as Dulbecco's Modified Eagle Medium (DMEM), fetal bovine serum (FBS), nonessential amino acids and antibiotics, and growth and morphogenic factors such as fibroblast growth factor (FGF), transforming growth factors (TGFs), vascular endothelial growth factor (VEGF), epidermal growth factor (EGF), insulin-like growth factor (IGF-1), bone morphogenetic growth factors (BMPs), nerve growth factors, and related proteins may be used. Growth factors are known in the art, see, e.g., Rosen & Thies, CELLULAR & MOLECULAR BASIS BONE FORMATION & REPAIR (R.G. Landes Co., Austin, Tex., 1995). Additional options for delivery via the silk include DNA, siRNA, antisense, plasmids, liposomes and related systems for delivery of genetic materials; peptides and proteins to activate cellular signaling cascades; peptides and proteins to promote mineralization or related events from cells; adhesion peptides and proteins to improve film-tissue interfaces; antimicrobial peptides; and proteins and related compounds.

Alternatively, the silk fibroin may be mixed with hydroxyapatite particles, see PCT/US08/82487. As noted herein, the silk fibroin may be of recombinant origin, which provides for further modification of the silk such as the inclusion of a fusion polypeptide comprising a fibrous protein domain and a mineralization domain, which are used to form an organic-inorganic composite. These organic-inorganic composites can be constructed from the nano- to the macro-scale depending on the size of the fibrous protein fusion domain used, see WO 2006/076711. See also U.S. patent application Ser. No. 12/192,588.

Silk fibroin can also be chemically modified with active agents in the solution, for example through diazonium or carbodiimide coupling reactions, avidin-biodin interaction, or gene modification and the like, to alter the physical properties and functionalities of the silk protein. See, e.g., PCT/US09/64673; PCT/US10/41615; PCT/US10/42502; U.S. application Ser. No. 12/192,588.

The silk optical components comprising active agents or biological materials may be suitable for long term storage and stabilization of the cells and/or active agents. Cells and/or active agents, when incorporated in the silk reflective components, can be stable (i.e., maintaining at least 50% of residual activity) for at least 30 days at room temperature (i.e., 22° C. to 25° C.) and body temperature (37° C.). Hence, temperature-sensitive active agents, such as some antibiotics, can be stored in silk optical films without refrigeration. Importantly, temperature-sensitive bioactive agents can be delivered (e.g., through injection) into the body in silk optical components and maintain activity for a longer period of time than previously imagined. See, e.g., PCT/US2010/026190.

The silk reflector devices can enhance the reflectivity even when integrated and operated in an irregular scattering and/or absorbing medium, such as a humid or wet scattering environments. This irregular scattering and/or absorbing medium may include any possible scattering medium known to one skilled in the art that the silk reflector device may be useful in. For example, the scattering medium may be an ambient environment, humid or wet environment, water, liquids, suspensions or gels, biological environment such as inside a biological body where the scattering medium may be a biological tissue or organ. Without resorting to coherent detection techniques or any contrast agents for enhancement, the reflectivity of the silk reflective component/device in these media possess enhanced reflectivity to about 10-300%, for instance, at least about 20%, at least about 40%, at least about 100%, at least about 150%, at least about 200%, or at least about 250%. The reflectivity of the silk reflective component/device in these media can therefore still be detected, with enhanced sensitivity, when the thickness of the scattering medium that blocks the detection source from the silk reflector is in the order of ~0.1 mm, ~1 mm, ~1 cm, and ~10 cm.

In one embodiment, the silk implantable reflector based on the silk-microprism array was used to enhance the intrinsic sensitivity to optically thick tissues without resorting to coherent detection techniques or any contrast agents for enhancement. Optically thick tissues, or deep tissues, can refer to those tissues that extend over distances much greater than the typical photon mean free path—which is longest in the red/near-infrared spectral region where it assumes values in the order of 0.1 mm for most soft tissues. For example, the optically thick tissues can be deeper than 200 μm. Having a reflecting element embedded within biological tissue would allow for the collection and redirection of forward scattered photons which are generally lost in widely used non-invasive imaging techniques. Matcher et al., 1997; Zonios & Dimou, 2009. Additionally, implantation of microprisms has attracted attention to increase contrast ratios in multiphoton microscopy by tailored redirection of light and rotation of the imaged layer planes. Chia & Levene, 102 J Neurophysiol. 1310 (2009).

The silk reflectors can also be used in an optical diagnostic situation involving light scattering, where specific spectral information from the volume under test is obtained and associated with physiological markers of interest. For example, silk reflectors can be used with different spectrally responsive elements, e.g., different spectral filters, for desired optical responses.

The silk reflective films provide a resorbable photonic component that adds optical functionality to living tissue without need for retrieval. The silk photonic devices can be designed in both micro- and nano-photonics to enter the human body and can be seamlessly, or relatively easily, incorporated as part of medical diagnostic systems. The approach also enables additional functionalities, such as deep tissue light delivery or relay of optical information either by enhancement of endogenous optical responses, increasing image contrast, or by offering ad-hoc spectral filtering.

Additionally, the material properties of silk allow for the coexistence of optical function and biological storage (Lu et al., 2010; Szybala et al., 219 Exp. Neurol. 126 (2009); Witz et al., 29 Biomaterials 3609 (2008)), leading to multifunctional photonic systems where functionalities, such as drug/therapeutic delivery, can also be incorporated into the optical implant. The lack of need to retrieve the photonic devices extends the utility of this material platform beyond medical applications into environmental monitoring or food chain safety where such devices can be used without negative impact on the environment or the consumer.

It can also be desirable to design a bio-integrated device, such as an implantable medical device, which has a large fraction of the device flexible to easily conform to the surface of a subject to be contacted with the implantable medical device. For example, the device may be fabricated from an ultrathin and flexible silk reflective film. Such implantable devices can hence form conformal contact with the curvilinear surfaces of various organs or tissues. Conformal contact of the bio-integrated device comprising the silk reflective component with a subject may be realized by contacting the device with aqueous solution, or a wet surface of the subject. In this regard, the silk film is at least partially dissolvable upon contact with the aqueous solution or the wet surface, so as to enable the conformal contact of the implantable device with the surface of the subject to be contacted with the implantable medical device. Each layer of silk film herein is typically no more than 100 μm, up to 75 μm, up to 25 μm, up to 7 μm, up to 2.5 μm, or up to 1 μm, to enable the fast dissolution upon contact with the aqueous solution or wet surface.

In some embodiments, the design of the bio-integrated device comprising the silk reflective film has a large fraction of the device soluble and/or biodegradable. Hence, the device will disappear or resorb, over time, rendering the devices biocompatible.

The dissolution time of the silk reflective components/device can also be tuned from days to months by controlling the degree of crystallinity during the fibroin protein self-assembly process. Jin et al., 15 Adv. Funct. Mater. 1241 (2005); Lu et al., 6 Acta Biomater. 1380 (2010). This can be accomplished by regulating the water content within the silk film through an annealing step to stabilize the device for prolonged operation in wet environments such as those encountered in the in vitro and/or in vivo studies.

The silk reflective film can be used in varieties of other applications. In one embodiment, the silk reflective films may be affixed to pharmaceuticals, food products or any editable novelty, or any packages, including holographic label. Similarly, the label itself may contain an active agent such as a pharmaceutical (e.g., an antibiotic). See, e.g., WO 09/155397.

In another embodiment, the silk reflective films can be fabricated into sensors and detectors, dielectric mirrors or coatings, imaging devices, or drug/therapeutic delivery device. For example, the silk reflective component embedded active agents (e.g., therapeutic agents) or biological materials are suitable for a biodelivery device. Techniques for using silk fibroin as a biodelivery device may be found, for example, in U.S. patent application Ser. No. 10/541,182; Ser. No. 11/628,930; Ser. No. 11/664,234; Ser. No. 11/407,373; PCT/US07/020789; PCT/US08/55072; PCT/US09/44117. Some embodiments of the present invention relate to the utility of silk-fibroin embedded therapeutic agents or biological materials as drug delivery systems for potential utility in medical implants, tissue repairs and for medical imaging devices.

The silk reflective film as a biodelivery vehicle may present a controlled-release of active agent. Controlled-release permits dosages to be administered over time, with controlled release kinetics. In some instances, delivery of the therapeutic agent or biological material is continuous to the site where treatment is needed, for example, over several weeks. Controlled-release over time, for example, over several days or weeks, or longer, permits continuous delivery of the therapeutic agent or biological material to obtain preferred treatments. The controlled delivery vehicle is advantageous because it protects the therapeutic agent or biological material from degradation in vivo in body fluids and tissue, for example, by proteases. See, e.g., PCT/US09/44117.

Controlled release of the bioactive agent from the silk reflective film may be designed to occur over time, for example, for greater than about 12 hours or 24 hours, inclusive; greater than 1 month or 2 months or 5 months, inclusive. The time of release may be selected, for example, to occur over a time period of about 12 hours to 24 hours, or about 12 hours to 1 week, inclusive. In another embodiment, release may occur for example on the order of about 1 month to 2 months, inclusive. The controlled-release time may be selected based on the condition treated. For example, a particular release profile may be more effective where consistent release and high local dosage are desired.

The silk reflective film may be combined with other silk-based drug-delivery constructs, including microspheres, pads, porous structures, or films. See, e.g., PCT/US09/44117.

The silk reflective components can also used in tissue engineering. For example, silk reflective film can be affixed to engineered tissue. Such techniques would further confer functionality to the engineered tissues, such as monitoring the implantation or any activities of the engineered tissues in vivo.

Embodiments of the invention also relate to compositions and processes for preparing silk reflectors comprising a multiple layers of silk films, each silk layer having the same or different reflective elements formed thereon.

In one embodiment, one or more silk layers have a different index of refraction than the others.

In one embodiment, one or more silk layers have a different thickness than the others.

The reflectivity of silk reflector may be modulated by modifying the thickness of the silk film, the index of refraction of the silk film, the embedding of active agent in the silk film, surface modification of the silk film by functional groups or chemical functionalization or generic modification of silk fibroin, conformation change or dissolution of silk film, and the like.

The reflectivity of silk reflector may also be modulated by number of layers of silk reflective film, the thickness of each silk film, the index of refraction of each layer of the multilayer silk film, embedding of different active agents in each layer of the multi-layer silk film, surface modification of the silk film by different functional groups or different modification strategies for chemical functionalization or generic modification of each layer of the multi-layer silk fibroin, conformation change or progressive dissolution of multi-layer silk film.

The invention will be further characterized by the following examples which are intended to be exemplary of the embodiments.

The present invention can be defined in any of the following numbered paragraphs:

A process for fabricating a silk reflector, comprising:
replicating from a master pattern having a reflective element or an array of reflective elements onto a surface of a silk film, wherein the reflective element comprises a microprism.

The process of paragraph 82, further comprising:
dispersing reflective particles in the silk film.

The process of paragraph 83, wherein the reflective particles are metal nanoparticles selected from the group of Au, Ag, and combinations thereof.

The process as in any one of paragraphs 82-84, further comprising:
stacking multiple layers of silk films having the reflective elements formed thereon.

The process of paragraph 85, wherein at least one silk layer has a different index of refraction from the others.

The process as in any one of paragraphs 85-86, wherein at least one silk layer has a different thickness from the others.

The process as in any one of paragraphs 82-87, further comprising:
adding at least one active agent to the silk film.

The process as in any one of paragraphs 82-87, further comprising:
functionalizing the silk film with an active group.

The process of paragraph 88 or 89, wherein the reflectivity of the silk reflector is modulated by the addition of the active agent to the silk film or functionalization of the silk film with the active group.

The process as in any one of paragraphs 82-90, further comprising:
wetting or dissolving at least part of the silk reflector to conform the silk reflector to the surface of a subject upon contact.

The process of paragraph 91, wherein the reflectivity of the silk reflector is modulated by partially dissolving the silk reflector.

A silk reflector comprising at least one layer of silk film, wherein a reflective element or an array of reflective elements is formed onto the surface of the silk film layer, and wherein the reflective element comprises a microprism.

The silk reflector of paragraph 93, further comprising reflective particles dispersed in the silk film.

The silk reflector of paragraph 94, wherein the reflective particles are metal nanoparticles selected from the group of Au, Ag, and combinations thereof.

The silk reflector as in any one of paragraphs 93-95, wherein the silk reflector comprises multiple layers of silk film, each silk film layer comprising the reflective element or an array of the reflective elements formed thereon.

The silk reflector of paragraph 96, wherein at least one layer has a different index of refraction from the others.

The silk reflector as in any one of paragraphs 96-97, wherein at least one layer has a different thickness from the others.

The silk reflector as in any one of paragraphs 93-98, further comprising at least one active agent in the silk film.

The silk reflector as in any one of paragraphs 93-98, wherein the silk film is functionalized with an active group.

The silk reflector as in any one of paragraphs 99-100, wherein the reflectivity of the silk reflector is modulated by addition of the active agent to the silk film or functionalization of the silk film with the active group.

The silk reflector as in any one of paragraphs 99-100, wherein the reflectivity of the silk reflector is modulated by releasing the active agent from the silk film or de-functionalization of the silk film.

The silk reflector as in any one of paragraphs 93-102, wherein the silk reflector is retroreflective.

The silk reflector as in any one of paragraphs 93-103, wherein the silk reflector has enhanced reflectivity when illuminated with a broadband light.

The silk reflector as in any one of paragraphs 93-103, wherein the silk reflector has enhanced reflectivity at specific wavelengths.

The silk reflector as in any one of paragraphs 93-105, wherein the intensity of reflectivity of the silk reflector has been enhanced about at least 40% when placed in an irregular scattering medium.

The silk reflector as in any one of paragraphs 93-105, wherein the intensity of reflectivity of the silk reflector has been enhanced about at least 300% when placed in an irregular scattering medium.

The silk reflector as in any one of paragraphs 106-107, wherein the scattering medium is ambient environment, water, liquids, suspensions, or gels, and wherein the thickness of the scattering medium blocking the silk reflector from the detection source is about 0-10 cm.

The silk reflector as in any one of paragraphs 106-107, wherein the scattering medium is a tissue or organ, and wherein the thickness of the scattering medium blocking the silk reflector from the detection source is about 0-2 mm.

An implantable silk reflector having optical utility for in vivo operation, comprising:
at least one layer of silk film having a reflective element or an array of reflective elements formed onto the surface of the silk layer,
wherein the reflective element comprises a microprism, and wherein the silk reflector is biocompatible and bioresorbable.

The implantable silk reflector as in any one of paragraphs 110, further comprising at least one active agent in the silk film.

The implantable silk reflector as in any one of paragraphs 110, wherein the silk film is functionalized with an active group.

The implantable silk reflector as in any one of paragraphs 110-112, wherein the reflectivity of the implantable silk reflector is modulated by addition of the active agent to the silk film or functionalization of the silk film with the active group.

The implantable silk reflector as in any one of paragraphs 110-112, wherein the reflectivity of the implantable silk reflector is modulated by releasing the active agent from the silk film or de-functionalization of the silk film.

The implantable silk reflector as in any one of paragraphs 110-114 wherein the reflectivity of the implantable silk reflector is modulated by partially dissolving the implantable silk reflector.

The implantable silk reflector as in any one of paragraphs 110-114, wherein the implantable silk reflector has enhanced reflectivity when illuminated with a broadband light.

The implantable silk reflector as in any one of paragraphs 110-115, wherein the implantable silk reflector has enhanced reflectivity at specific wavelengths.

The implantable silk reflector as in any one of paragraphs 110-117, wherein the intensity of reflectivity of the implantable silk reflector has been enhanced about at least 40% when placed in an tissue or organ, wherein the thickness of the tissue or organ blocking the implantable silk reflector from the detection source is about 0-2 mm.

The implantable silk reflector as in any one of paragraphs 110-117, wherein the intensity of reflectivity of the implantable silk reflector has been enhanced about at least 300% when placed in an tissue or organ, wherein the thickness of the tissue or organ blocking the implantable silk reflector from the detection source is about 0-2 mm.

A dielectric mirror comprising the silk reflector as in any one of paragraphs 96-119.

An optical label comprising the silk reflector as in any one of paragraphs 93-119.

A biosensing device comprising the silk reflector as in any one of paragraphs 93-119.

An implantable device comprising the silk reflector as in any one of paragraphs 93-119.

An imaging device comprising the silk reflector as in any one of paragraphs 93-119.

A drug delivery device comprising the silk reflector as in any one of paragraphs 93-119.

The present invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

EXAMPLES

Example 1

Preparation of Silk Fibroin Solution

Production of silk fibroin solutions has been described previously. Perry et al., 2008; McCarthy et al., 54 J. Biomed. Mats. Res. 139 (2001). Briefly, sericin, a water-soluble glycoprotein bound to raw fibroin filaments, was removed from the silk strands by boiling B. mori cocoons in a 0.02 M aqueous solution of $NaCO_3$ for 60 min. Thereafter, the remaining silk fibroin bundle was rinsed thoroughly in purified water and allowed to dry overnight. The dry fibroin bundle was then dissolved in a 9.3 M aqueous solution of LiBr at 60° C. for 4 hr. The LiBr salt was then extracted from the solution over the course of three days, through a water-based dialysis process using Slide-A-Lyzer® 3.5K MWCO dialysis cassettes (Pierce, Rockford, Ill.). Any remaining particulates were removed through centrifugation and syringe-based micro-filtration (5 μm pore size, Millipore Inc., Bedford, Mass.). This process can yield 8%-10% (w/v) silk fibroin solution with minimal contaminants and reduced scattering for optical applications.

The silk fibroin solution may be concentrated, for example, to about 30% (w/v), if desired. See, e.g., WO 2005/012606. Briefly, the silk fibroin solution with a lower concentration may be dialyzed against a hygroscopic polymer, such as PEG, amylose or sericin, for a time period sufficient to result in a desired concentration.

Additionally, silk fibroin solution can be combined with one or more biocompatible polymers such as polyethylene oxide, polyethylene glycol, collagen, fibronectin, keratin, polyaspartic acid, polylysin, alginate, chitosan, chitin, hyaluronic acid, and the like; or one or more active agents, such as cells, enzymes, proteins, nucleic acids, antibodies and the like, as described herein. See, e.g., WO 04/062697 and WO 05/012606. Silk fibroin can also be chemically modified with active agents in the solution, for example through diazonium or carbodiimide coupling reactions, avidin-biodin interaction, or gene modification and the like, to alter the physical properties and functionalities of the silk protein. See, e.g., PCT/US09/64673; PCT/US10/41615; PCT/US10/42502; U.S. application Ser. No. 12/192,588.

Example 2

Fabrication of Silk Reflector Films

Figure 2:
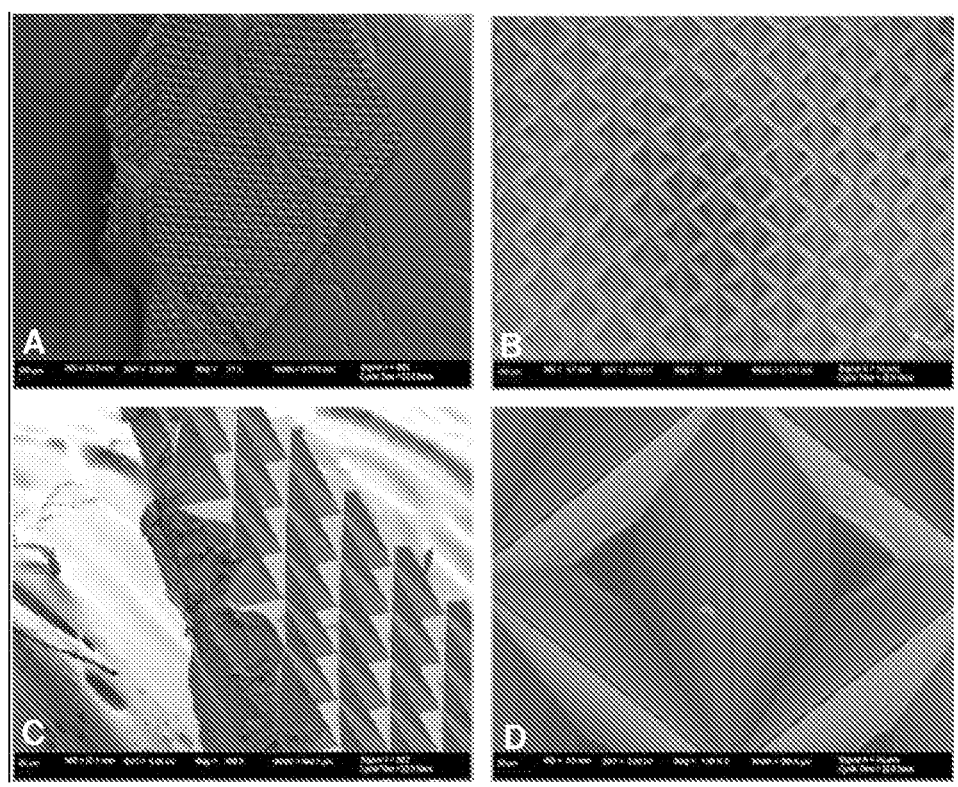
FIGS. 2A-2D are scanning electron microscope images showing the different magnifications of the prisms of the silk reflector.

The fabrication of the silk reflector films was obtained by using a casting technique similar to soft-lithography. Perry et al., 2008; Xia & Whitesides, 1998. Briefly, silk fibroin solution of excellent optical quality and stability was cast onto a microprism master mould (3M™ SCOTCHLITE™ Reflective Material—High Gloss Film, 3M, St. Paul, Minn.). The master consists of an array of microprisms, which have dimensions of about 100 micrometers and clustered in groups as shown in FIG. 1 and FIG. 2.

Figure 5:
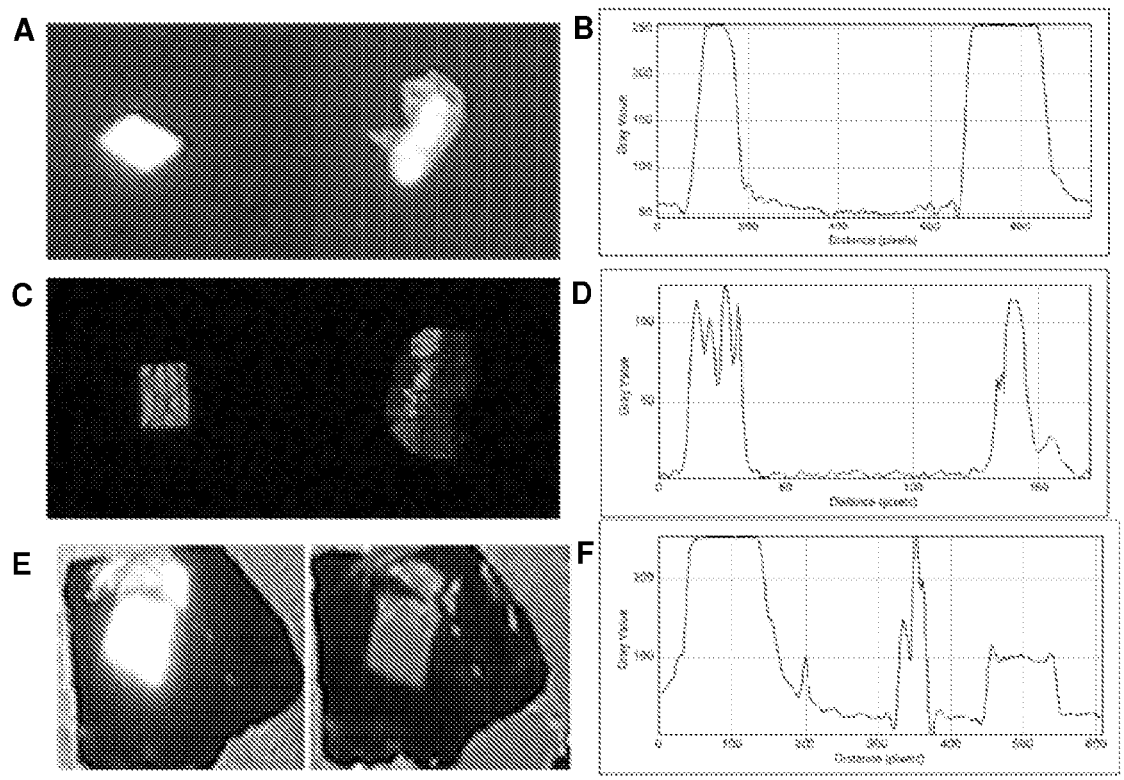
FIGS. 5A-5F show the results of reflectivity measurement from the setup illustrated in FIG. 4.
Figure 6:
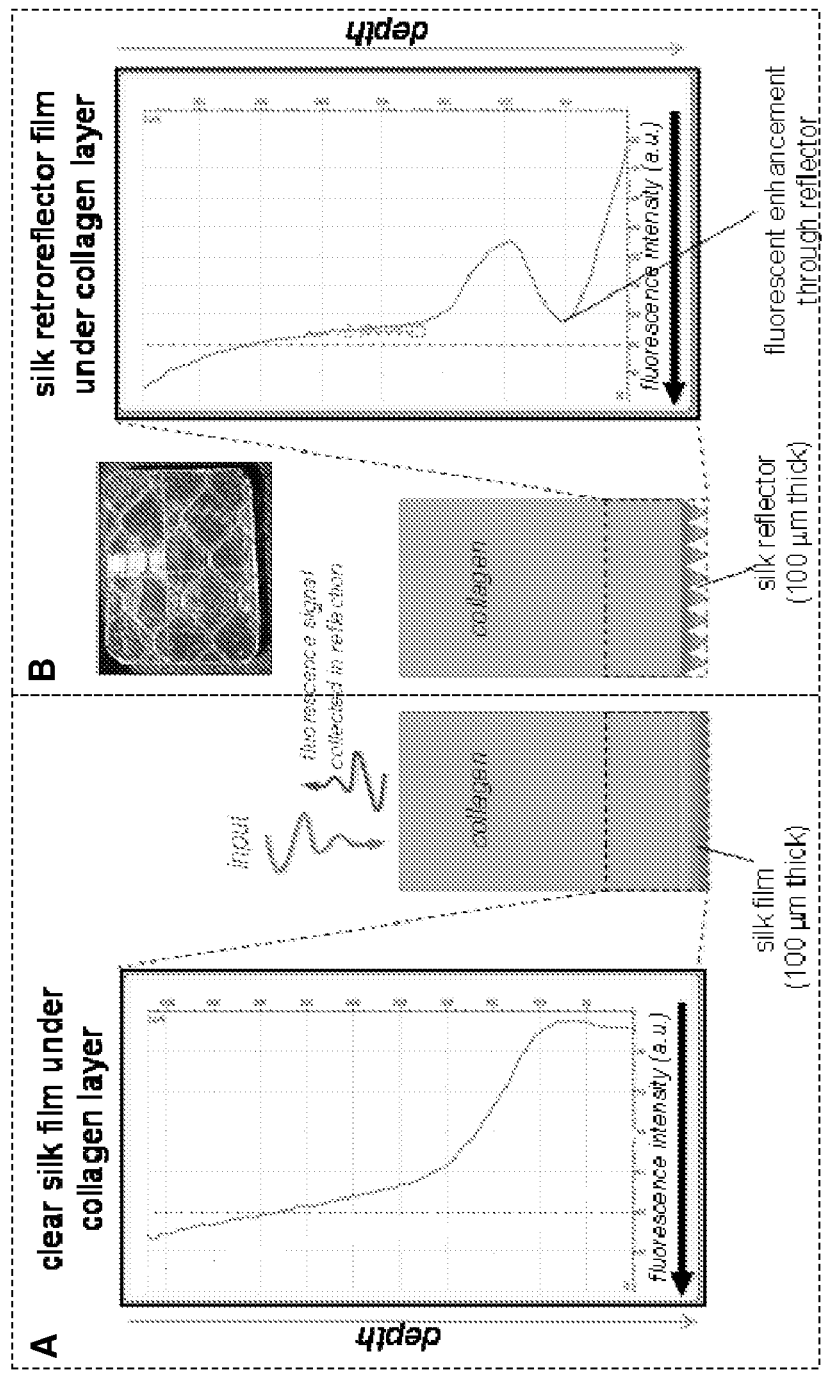
FIGS. 6A and 6B show the comparison of the detection of a clear silk film (FIG. 6A) versus the detection of a reflector silk film (FIG. 6B) underneath of a 3 mm collagen layer.

The silk solution was allowed to dry and crystallize for 8-12 hours, upon which it was mechanically detached from the master surface. Upon microscopic examination, the silk retroreflective films replicate the master and have a reflective appearance similar to the master mould, as shown in FIG. 5. The index of refraction of silk is n=1.54. The silk films were water annealed to guarantee reduced solubility in a humid environment without loss of function.

Additionally, the silk film may be activated, for example, by polyethylene glycol (see, e.g., PCT/US09/64673) and/or loaded with an active agent and cultured with organisms, in uniform or gradient fashion. See, e.g., WO 2004/0000915; WO 2005/123114; U.S. Patent Application Pub. No. 2007/0212730. Other additives, such as polyethylene glycol, PEO, or glycerol, may also be loaded in the silk film to alter features of the silk film, such as morphology, stability, flexibility, and the like. See, e.g., PCT/US09/060135.

Example 3

Reflection Measurements

The retroreflecting silk film were characterized by measuring the luminous intensity and retroreflector coefficients per illuminance level on the surface of the retroreflector (in candelas/1× and candelas/(1×/m$^2$), respectively).

Figure 3:
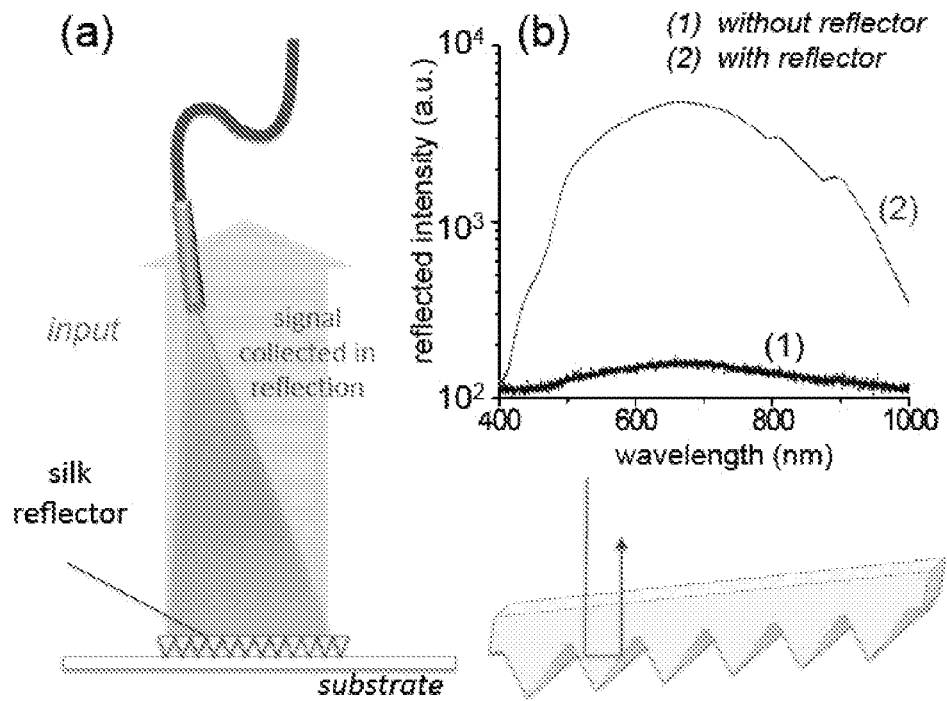
FIG. 3A is a schematic of the experimental setup for the evaluation of the performance of replicated microprism silk reflectors.
FIG. 3B is a graph showing the result of the performance of the silk microprism reflector, indicating orders of magnitude increase in the reflected signal compared to the background signal. Incoherent white light illumination was provided to the silk reflector from a fixed height and a back-scattering reflection probe was used to collect the response from the same height and couple it to a spectrometer.

The performance of the replicated silk films as reflectors was quantified by exposing the system to a quasi-isotropic illumination provided by a white light source (e.g., a flash light bulb). The reflection from the silk films was collected at a distance of 1.5 meters with a digital CCD camera, as shown in FIG. 3 and FIG. 7.

Figure 4:
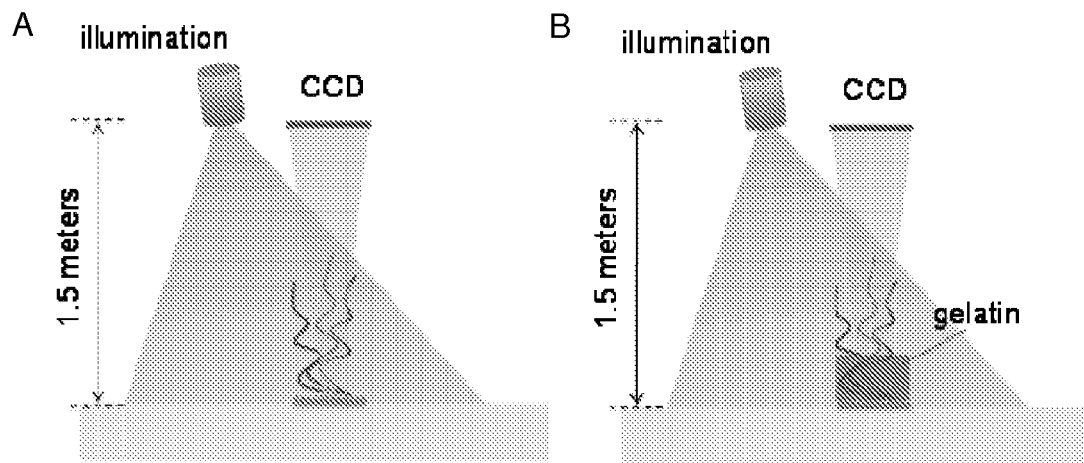
FIGS. 4A and 4B are schemes depicting the experimental setup used to establish the efficacy of both bare silk retroreflective films (FIG. 4A) and silk retroreflective films underneath a layer of scattering medium (e.g. gelatin) (FIG. 4B).
Figure 7:
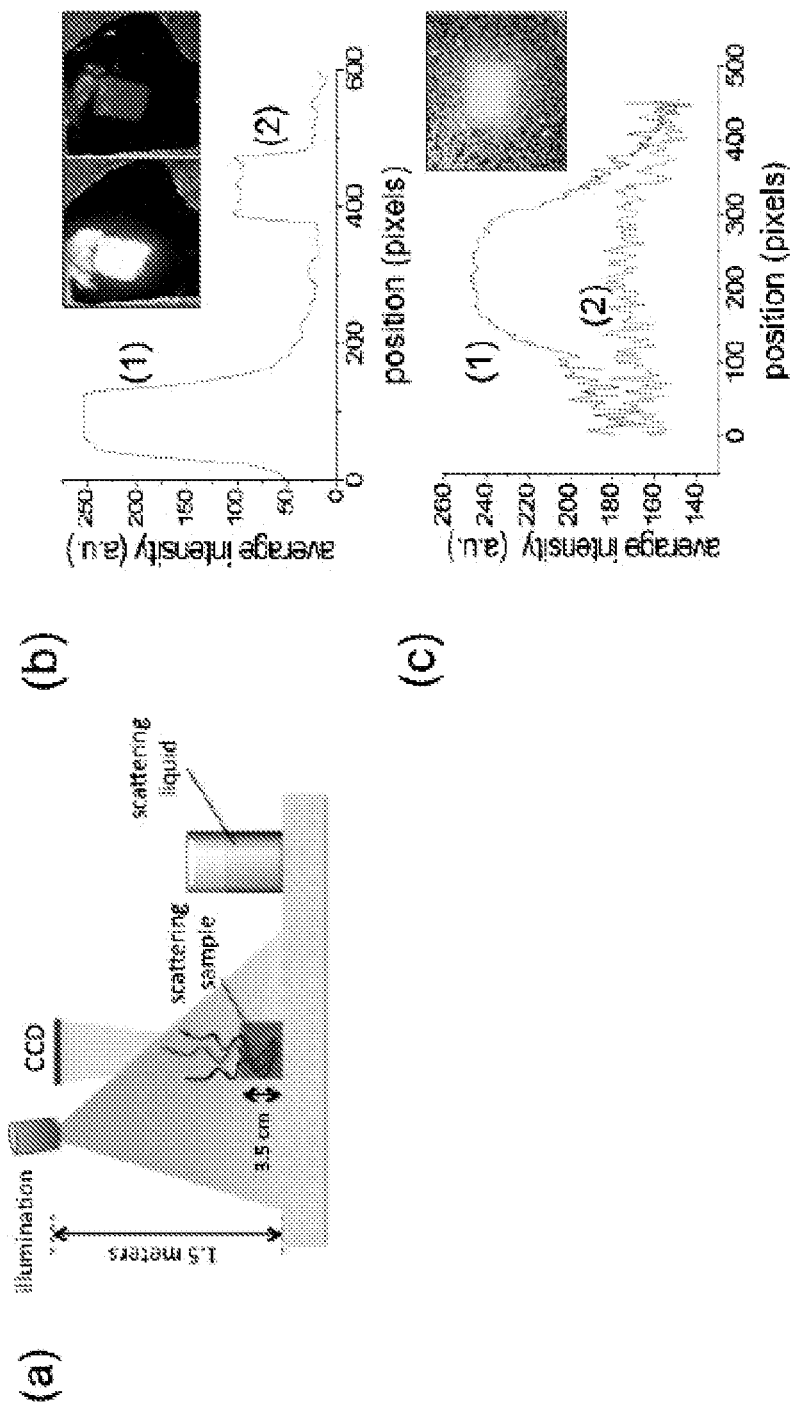
FIGS. 7A-7C show the results of silk retroreflectors embedded in scattering media.

The experimental setup for measuring the increase in reflected signal is illustrated in FIG. 4 and FIG. 7. For example, in FIG. 7, the reflectivity measurements were performed by using a white light source. A red filter was applied to the white light source to reduce the spectral range, thus avoiding CCD saturation. The reflectivity was characterized for both the silk film replica and the master. In both cases, the images were analyzed by acquiring the average of multiple lineouts of the intensity values collected by the CCD chip at the image plane. The values collected in reflection from the master and the silk replicas were found to be in agreement, with a reflection coefficient (defined as the ratio of the coefficient of luminous intensity of a plane retroreflecting surface to its area expressed in candelas per square meter) in excess of 300 (e.g., between 300 and 400). See, e.g., FIG. 5. Hence such silk retroreflective films can be used for broad angle reflection in, e.g., safety clothing and garments.

The annealing process (i.e., to make silk films insoluble in water) may cause some loss of flatness in the surface of silk films, thereby causing some variation in the surface reflectivity. This loss of flatness may be ameliorated by making the silk film thicker, e.g., above 20 μm.

Example 4

Animal Experiments

Female Balb/c mice (6-8 weeks old) were anesthetized with an intraperitoneal injection of a ketamine/xylazine mix. Depth of anesthesia was monitored by palpebral and withdrawal reflexes to confirm that the animal had reached "stage 3" of anesthesia. Once the animal was lightly anesthetized, the back was shaved and cleaned at the incision site with 70% ethanol, followed by a betadine surgical scrub. Once stage 3 was confirmed, a small longitudinal incision was made through the skin and the sterile implants (ethylene oxide sterilized) were inserted. The incision was closed with a Dexon 5-0 suture. The animal was monitored until ambulatory and given a dose of analgesia (e.g., Buprenorphine subcutaneously) once surgery was completed.

Example 5

Performance of Silk Reflectors

The performance of the silk microprism reflectors were evaluated, as shown in FIG. 3, indicating orders of magnitude increase in the reflected signal compared to the background signal. The silk reflectors were also characterized by comparing their optical performance to that of the master pattern. The device was evaluated by monitoring the diffuse reflected light under isotropic illumination. In general, the silk reflector replicated the master pattern faithfully and its optical performance matched that of the master pattern, providing orders of magnitude of measured increase in the diffuse reflection when compared to the background (FIG. 3 and FIG. 5).

The performance of silk reflectors under humid or wet scattering environments were assessed by placing the silk reflector films under a 4 cm thick block of gelatin or submerged in a talcum powder and water suspension at a depth of 6.5 cm. Such conditions were used to mimic an irregular scattering medium. In both cases, the presence of the silk reflector resulted in a significant enhancement of signal at the detector plane, and an increased the backscattered signal intensity by several orders of magnitude, allowing an easy imaging, or relatively easy imaging, by using the silk reflectors in the media. See also FIGS. 4 to 7.

The silk reflectors can also be used in an optical diagnostic situation involving light scattering, where specific spectral information from the volume under test is obtained and associated with physiological markers of interest. For example, silk reflectors can be used with different spectrally responsive elements, e.g., different spectral filters, for desired optical responses.

Figure 8:
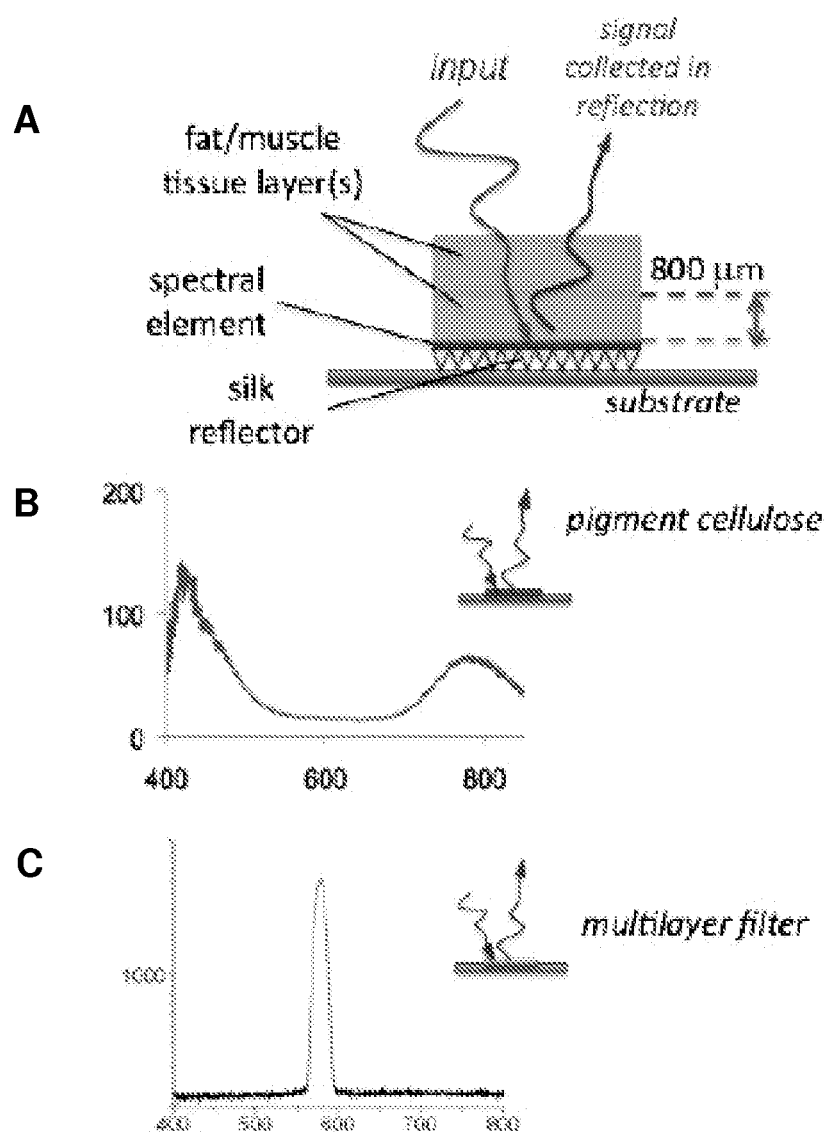
Figure 9:
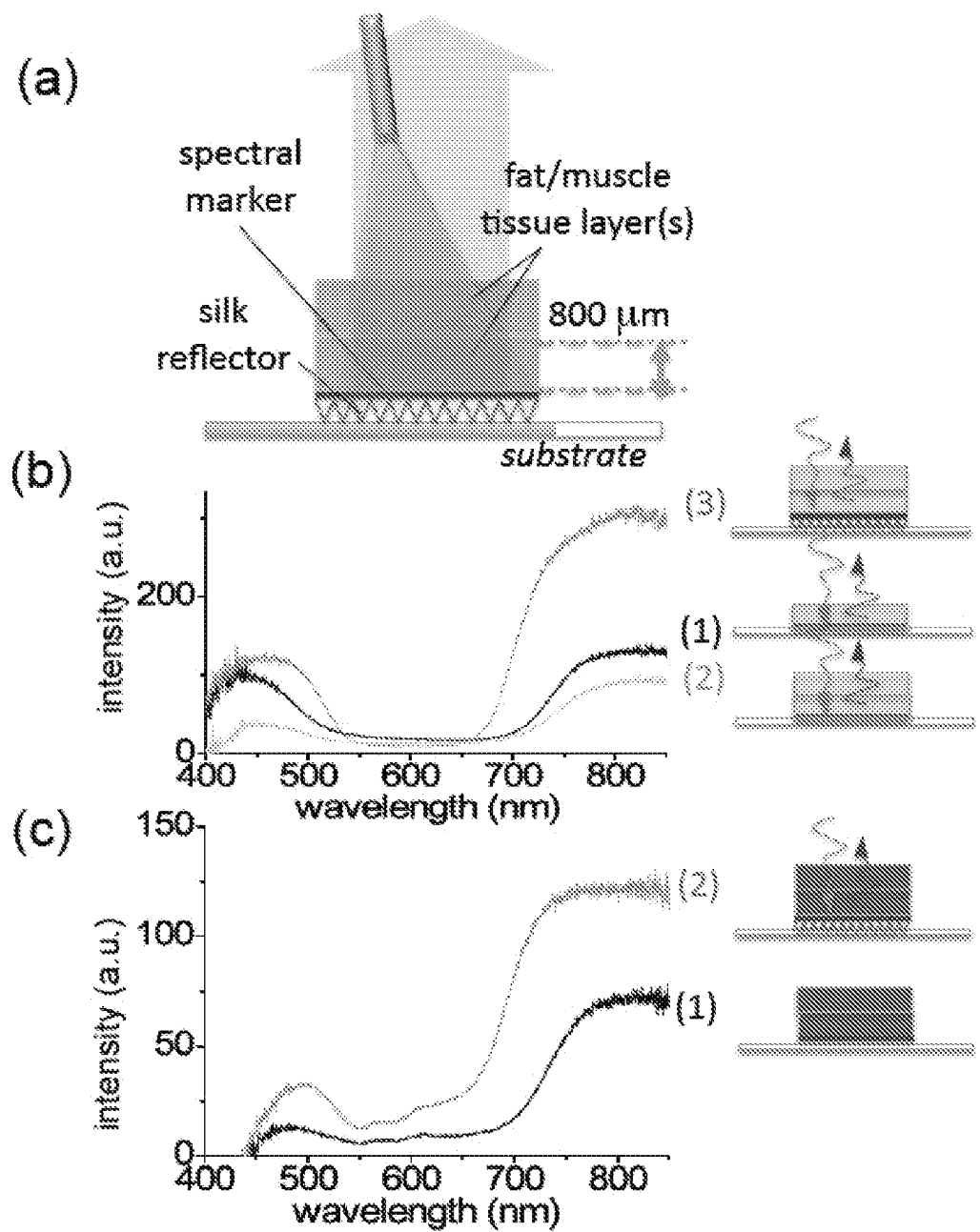
FIGS. 9A-9C show the results from in vitro experiments with incoherent illumination and detection through a fiber probe of the backscattered spectrum from deep tissue layers.

Two spectrally responsive elements embedded in biological tissue were used and an in vitro experiment was performed to assess the variation in the optical response when the silk reflector device was present. As shown in FIGS. 7 to 9, the silk reflector was placed underneath two types of spectral filters: a 10 nm bandpass multilayer filter (with central wavelength $\lambda_0=630$ nm) and a layer of cellulose embedded with red pigment. These were chosen to provide known broadband and narrowband spectral responses to embed in tissue constructs to test the efficacy of the device. The reflector/spectral element was then covered either by single or multiple layers of 800-micrometer thick porcine fat or muscle tissue (FIG. 9). The resulting structure was then probed by illumination with incoherent white light delivered through a multimode fiber. The latter is part of a fiber-backscattering probe which acts as the collector for the diffuse retroreflected scattering signal and redirects it to a spectrometer.

Figure 10:
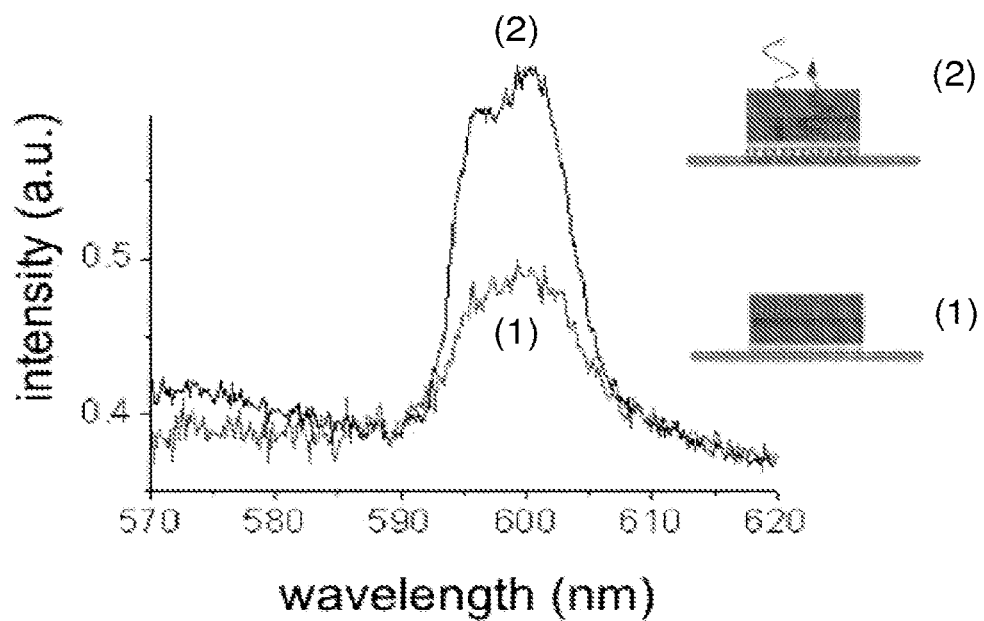
FIG. 10 shows the results from in vitro experiments with incoherent illumination and detection through a fiber probe of the backscattered spectrum through porcine muscle tissue layers in the presence of a multilayer filter (1) and resulting enhancement of the detected response with the addition of a silk microprism array (2).

Backscattering measurements (FIG. 9B) in the presence of one layer of adipose tissue revealed a broadband absorption attributed to the pigmented layer inserted underneath the tissue. The signal intensity decreased upon addition of a second layer, maintaining its overall spectral response at the expense of signal dynamic range. Insertion of the silk reflector underneath the structure in this case caused a significant increase in the backscattered signal collected and in the signal dynamic range, which is more representative of the true spectral response of the pigmented layer (FIG. 7). A similar increase (FIG. 9C) in detected signal and dynamic range with respect to the reflectorless case was encountered using muscle tissue where the filter broadband absorption again was revealed along with the spectral features of myocytes and a principal spectral peak at 620 nm. The same experiment was repeated by inserting in the tissue construct the narrowband (=10 nm) bandpass filter and, similarly, detecting an increase in the detected response over the bandwidth of the device (see also FIGS. 8 and 10). These results indicated the efficacy of operation of the silk reflector device in an in vitro environment with a tissue thickness ~1 mm.

Figure 11:
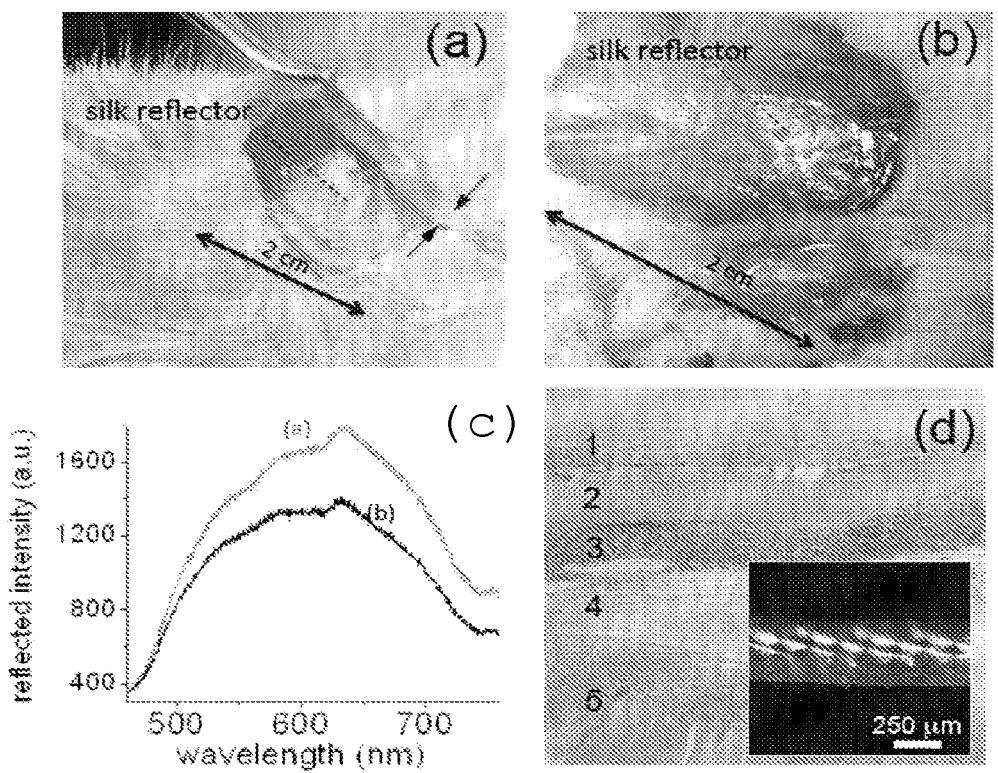
FIGS. 11A-11D illustrate the in vivo results by using the silk reflectors.
Figure 12:
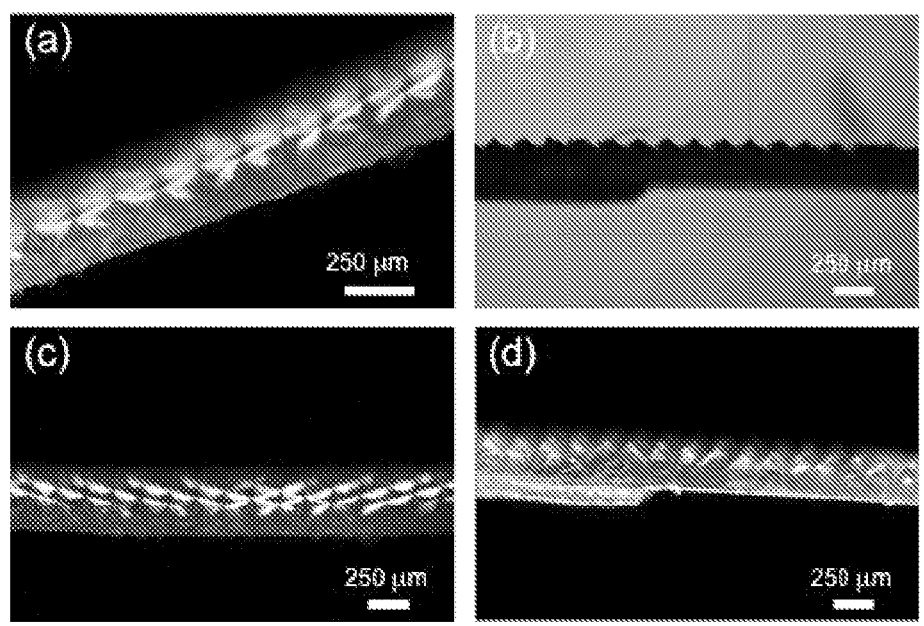
FIGS. 12A-12D show the microscope images of the silk reflectors used for the implants.

The silk reflectors can be used in vivo as an implantable device. In one embodiment, in vivo studies were conducted by implanting the silk reflector structures in Balb/c mice. The experiments were pursued in accordance with institutional IACUC-approved protocols. A ~1 cm×1 cm silk microprism reflector film having a thickness of approximately 100 μm was sterilized by ethylene oxide and then inserted subcutaneously through an incision on the back of the mouse. After suturing the wound site, the scattered signal was measured in the same fashion as described above. FIG. 11 illustrates the insertion of the device, and a corresponding set of measurements of the backscattered radiation. As shown in FIG. 11, comparison between the backscattered illumination through the mouse skin collected by the fiber probe at the implant site with control sites revealed a consistent improvement in collected signal of ~40% when compared to an adjacent, implantless site on the mouse. To interpret the experimental results, Monte Carlo model was used to solve the radiative transfer equation, an integro-differential equation widely used for describing light propagation in random media such as biological tissues. Ishimaru, WAVE PROPAGATION & SCATTERING IN RANDOM MEDIA, (Wiley-IEEE Press, 1997).

The above approach was used to calculate the backscattered signal intensity in the presence of the silk reflector. In the simulation, the silk reflective device was assumed to provide 100% reflectivity and to be located at a depth of 1.5 mm under the skin's surface. The simulations were evaluated two different values of the scattering coefficient ($\mu$=10, 15 mm$^{-1}$) and five different values of the absorption coefficient ($\mu_a$=0.005, 0.02, 0.015, 0.02, 0.03 mm$^{-1}$), typical of skin and muscle tissues in the NIR wavelength range (650-850 nm). The simulations showed a predicted increase in reflected signal which is in excellent agreement with what is observed experimentally both for the in vitro and in vivo cases. The details of MC simulations are described in Example 5.

Figure 13:
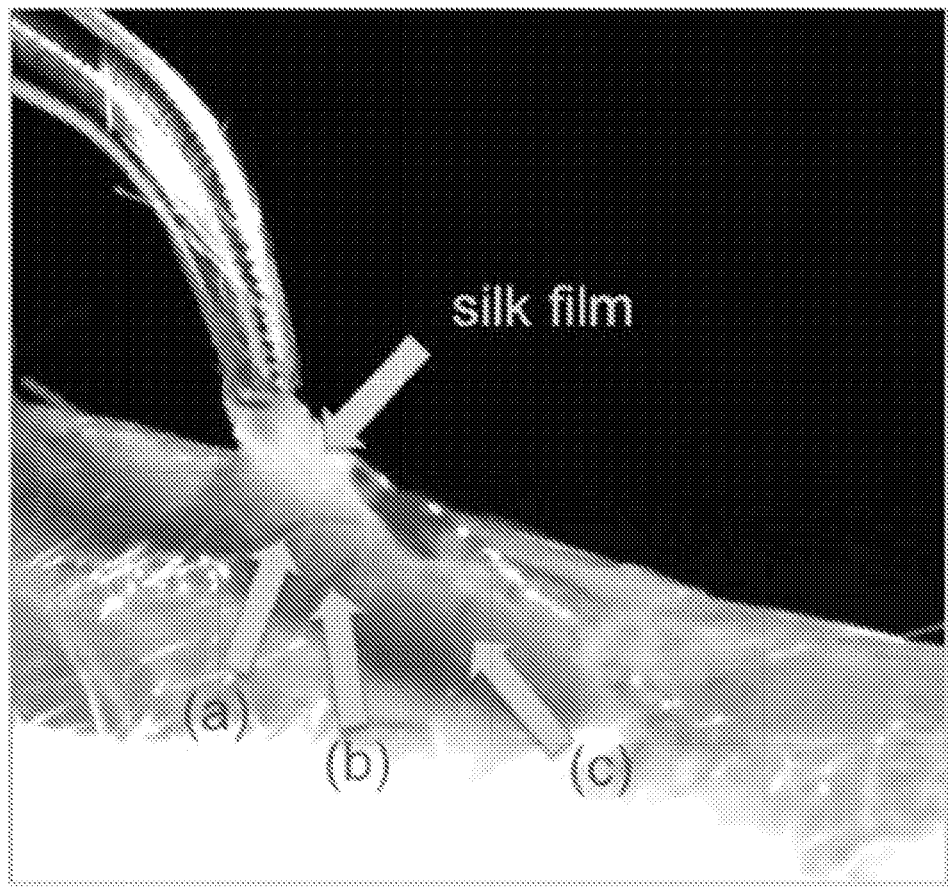
FIG. 13 shows the post implant analysis of the silk implant after 4 weeks of in-dwelling within the mouse. The arrows associated to (a), (b) and (c) indicate the revascularization occurring around the implanted film.
Figure 14:
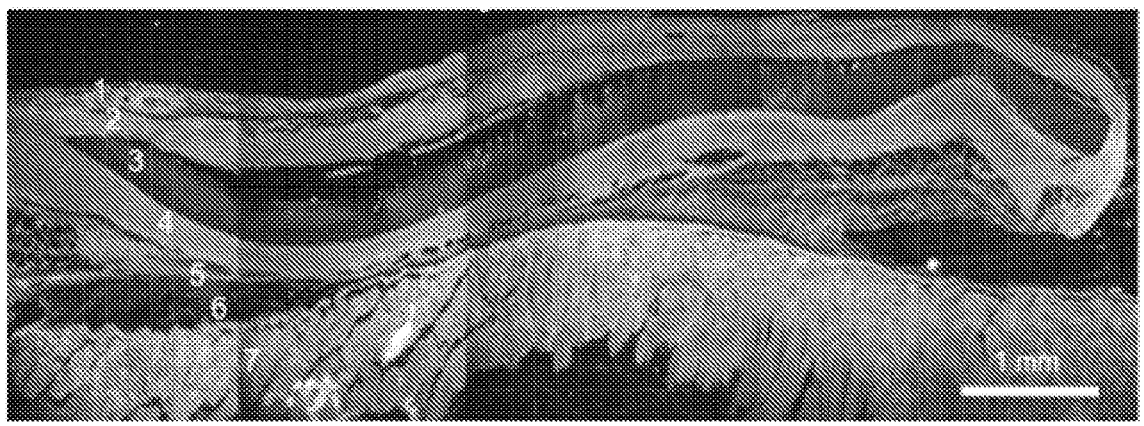
FIG. 14 shows the full darkfield microscopy image of histological cross section of the 1 cm reflector implanted in the mouse (after 4 weeks of implantation time). Visible are the outer epidermis layer (1) and subcutaneous tissue (2), the silk film, with the microprisms visible (3) the subcutaneous tissue (4,5 and 6), and muscle tissue (7). The subcutaneous tissue shows a thickening of the hypodermis directly under the implant (3) when compared to deeper hypodermis (4). The subcutaneous fat layer is unaffected (5).

The silk reflector devices were also monitored for adverse reactions and resorbability. No visible inflammation was found over 4 weeks and this was confirmed by histopathological sections of the implanted silk reflective film and the underlying tissue. The silk reflector was observed to alter in size over four weeks and initial stages of re-incorporation of the silk reflector into the tissue matrix was also observed over this time frame, such as revascularization on the surface of the silk film, were observable upon examination of the excised tissue. See, e.g., FIG. 13. The profile of the silk microprism arrays may be identified in the histological sections. See, e.g., FIG. 14. Implantation of degradable photonics can be achieved through the use of materials (such as silks) that cause no detrimental biological effects, and also retain desired functions for an extended period of time as they are reabsorbed. Additionally, silk devices were also demonstrated to present controlled degradation in vivo in support of these observations. Wang et al., 29 Biomats. 3415 (2008).

Example 6

Theoretic Modeling (a) The Radiative Transfer Equation

The Radiative Transfer Equation (RTE) is written as:

$$\frac{1}{v}\frac{\partial I(\vec{r},\hat{s},t)}{\partial t} + \hat{s}\cdot\vec{\nabla}\,I(\vec{r},\hat{s},t) + \mu_t I(\vec{r},\hat{s},t) = \mu_s\int_{4\pi}p(\hat{s},\hat{s}')I(\vec{r},\hat{s}',t)\,d\Omega' + S(\vec{r},\hat{s},t) \quad (1)$$

The RTE is an integro-differential equation that is widely used for describing light propagation in random media (such as biological tissues). Ishimaru, 1997. It is derived from general principles of energy balance at a microscopic level.

In Eq. (1), $I(\vec{r},\hat{s},t)$ is the specific intensity (or Irradiance), which is the number of photons per unit area, unit time and unit solid angle, found at time t in the position $\vec{r}$ along the direction $\hat{s}$; v is the speed of light in the medium; $\mu_s$ and $\mu_t$ are the scattering and total extinction coefficient, respectively, where $\mu_t=\mu_s+\mu_a$, and $\mu_a$ is the absorption coefficient; $p(\hat{s},\hat{s}')$ is the phase function, which represents the probability density per unit solid angle that a photon traveling along $\hat{s}'$ is scattered along $\hat{s}$; the phase function is assumed to depend only on the product $\hat{s}'\cdot\hat{s}$ (scattering angle θ); and $S(\vec{r},\hat{s},t)$ is a source term, which is the number of photons per unit time, unit volume and unit solid angle, generated at time t in the point $\vec{r}$ along the direction $\hat{s}$.

In Eq. (1), it is assumed that only photons in a narrow frequency band are traveling in the medium (i.e. scattering must be elastic). Eq. (1) is written in scalar form herein, although it can also be written in vectorial form to describe propagation of polarized or partially polarized light, in which case the specific intensity must be replaced by a vector which components are the Stokes parameters. Ishimaru, 1997.

(b) The Monte Carlo Method

To better describe the experimental results, a Monte Carlo (MC) code was used to solving the RTE. Monte Carlo is a stochastic method which solves Eq. (1) by direct simulation of the actual propagation of photons in random media according to well-established statistical laws. Zaccanti et al., 3 Pure Appl. Opt., 897-905 (1994). The core of MC code is a subroutine for the extraction of random numbers uniformly distributed in the interval (0, 1). By using a triplet of random numbers ($w_1$, $w_2$, $w_3$), the location of a scattering event can be updated in the 3D space, once the coordinates of the previous scattering event are known. It is assumed that the trajectory between the two consecutive scattering events is a segment of straight line. A random number $w_1$ can be arbitrarily chosen to define the pathlength L between the scattering events and $w_2$, $w_3$ can be used to define the azimuthal and the scattering angle $\phi$ and $\theta$, respectively. The pathlength L and the direction of the free flight between two consecutive scattering events were defined by the equations:

$$L = -\frac{1}{\mu_s}\ln(w_1); \Phi = 2\pi w_2; w_3 = 2\pi \int_0^{\theta} p(\theta')\sin(\theta')d\theta' \quad (2)$$

The last equality of Eq. (2) (where $\theta'=\hat{s}'\cdot\hat{s}$) can be inverted (in order to find $\theta(w_3)$) by resorting to numerical methods. Starting from the coordinates of the point where the photons are injected into the medium, the coordinates of each scattering event while the photon is moving in the medium can be calculated. This procedure was repeated until the photon's trajectory either intersects a specified area at the boundary of the medium where one or more detectors are located (useful or detected photon) or escapes from the medium (lost photon). Whenever the photon's trajectory intersects the boundary of the medium, reflections can also be taken into account due to the refractive index mismatch between diffusing and surrounding medium. This was done by comparison of a newly extracted random number ($w_4$) with the reflection coefficient of unpolarized radiation ($r_t$) (Born & Wolf, PRINCIPLES OF OPTICS (Pergamon Press, 1987)):

$$r_t = \frac{1}{2}\left\{\left[\frac{tg(\theta_i - \theta_t)}{tg(\theta_i + \theta_t)}\right]^2 + \left[\frac{\sin(\theta_t - \theta_i)}{\sin(\theta_t + \theta_i)}\right]^2\right\} \quad (3)$$

In Eq. (3), $\theta_t$ and $\theta_i$ are the transmitted and incident angle, respectively, calculated with respect to a direction perpendicular to the boundary at the point of intersection. If $w_4 < r_{tot}$, the photon is reflected and the new direction is calculated according to the formula $\theta_r$ and $\theta_i$, where $\theta_r$ is the angle of reflection; if $w_4 > r_{tot}$, the photon exits the medium and the trajectory is terminated. By using the same method, discontinuities in the refractive index within the random medium can also be considered. The above described statistical rule (Eq. 2), so called "White Monte Carlo," was run for the case of a non-absorbing medium.

Afterwards, the effect of the absorption coefficient was considered through the microscopic Beer-Lambert law: if a photon is detected after having traveled a total pathlength l through a non-absorbing medium, the probability to detect the same photon when the medium is absorbing is: $\exp(-\mu_a l)$. Therefore the effect of absorption was considered through re-scaling the weights of collected photons according to their pathlengths. For the phase function, even though many choices are possible, the Henyey-Greenstein phase function is widely adopted in studying the light propagation in biological tissues:

$$p(\theta) = \frac{1}{4\pi} \cdot \frac{1-g^2}{[1+g^2-2g\cos(\theta)]^{3/2}} \quad (4)$$

In Eq. (4), "g" is the asymmetry parameter: $g=<\cos(\theta)>$, which typically has a value larger than 0.8 (high probability of forward scattering) in biological tissue. The phase function was normalized to "1" over the entire solid angle ($4\pi$ steradians). More details on the Monte Carlo method can be found in references. See, e.g., Wang et al., 47 Computer Methods & Programs Biomed. 131-46 (1995); Martelli et al., LIGHT PROPAGATION THROUGH BIOLOGICAL TISSUE & OTHER DIFFUSIVE MEDIA: THEORY, SOLUTIONS, & SOFTWARE, (SPIE Press, 2009).

Applying the Models to Interpret Experimental Results

For MC simulations of the mouse experiment, two different values of the scattering coefficients ($\mu_s$=10, 15 mm$^{-1}$) and five different values of the absorption coefficients ($\mu_a$=0.005, 0.02, 0.015, 0.02, 0.03 mm$^{-1}$), typical of skin and muscle tissues in the NIR wavelength range (650-850 nm), were used. For the simulation of the adipose tissue experiment, lower values of the absorption coefficient ($\mu_a$=0.002, 0.003, 0.004, 0.005 mm$^{-1}$) and scattering coefficient ($\mu_s$=5 mm$^{-1}$) were chosen. This value of the scattering coefficient is typical, for instance, of breast tissue, which has a large component of fat.

Figure 15:
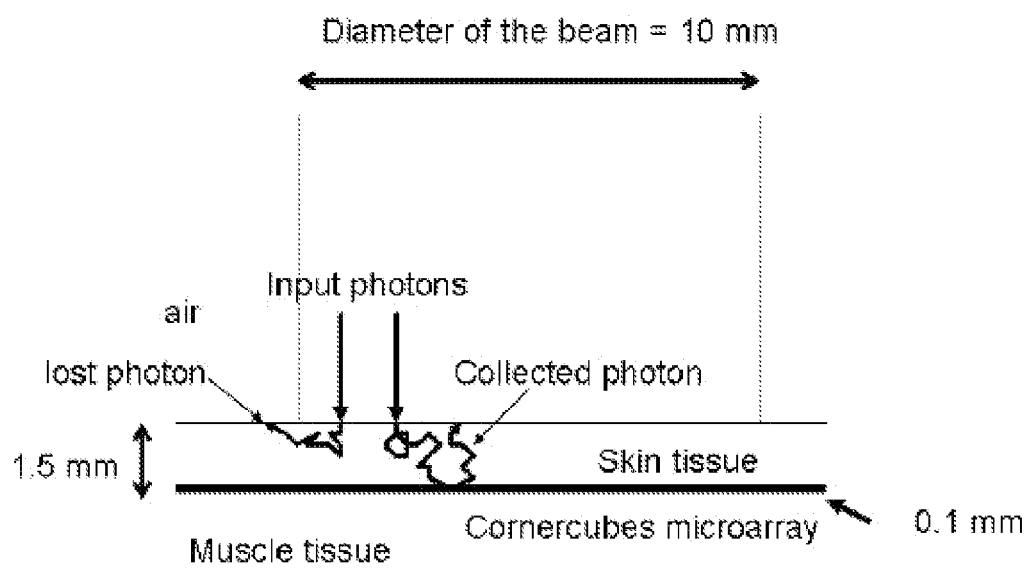
FIG. 15 is a schematic showing the geometry of the medium used for the Monte Carlo simulation for the mouse experiments and the adipose tissue experiments. In the latter case the distance of the cornercubes microarray from the surface of the tissue was 1 mm. Total reflection is considered at the skin-array (or fat-array) interface.

In both cases, Henyey-Greenstein phase function with asymmetry parameter g=0.9 was chosen to describe the single scattering event. The photons were collected on a FOW of 90° in the same area defined by the input cylindrical beam, as shown in FIG. 15.

Figure 16:
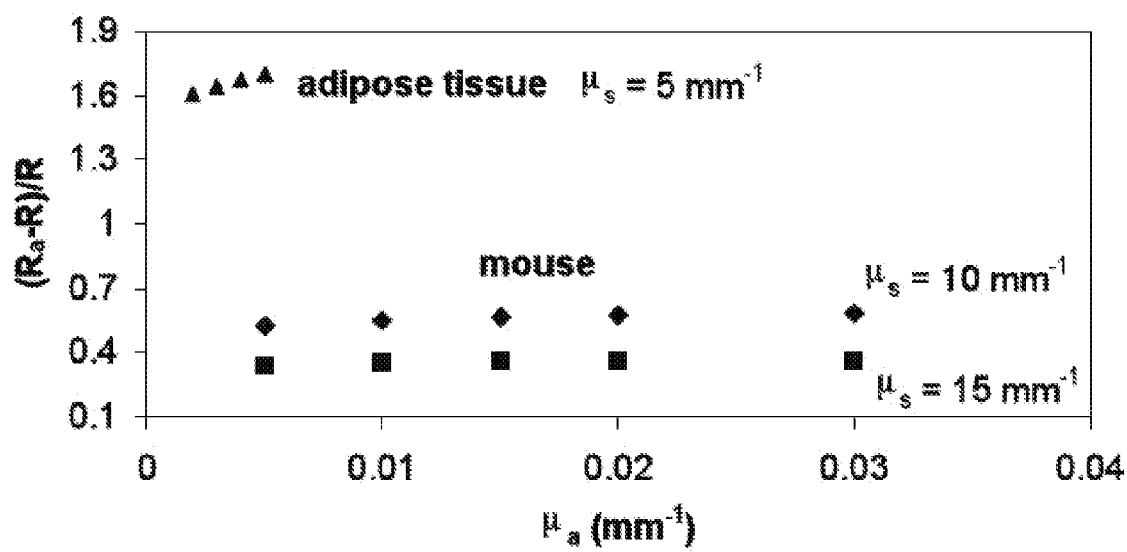
FIG. 16 is a graph showing the relative change of reflected power when the cornercubes microarray is present ($R_a$) or absent (R) in tissue, plotted against the absorption coefficient.
Figure 17:
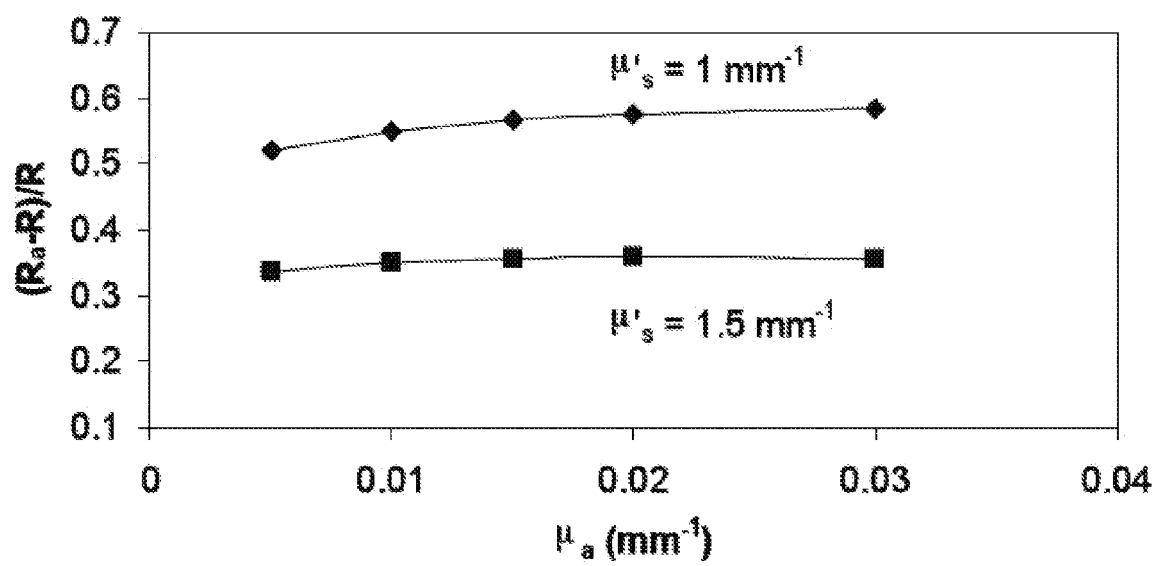
FIG. 17 is a graph showing the relative change of reflected power when the cornercubes microarray is present ($R_a$) or absent (R) in tissue, plotted against the absorption coefficient.

The relative increases of the reflected power between two scenarios for were plotted in FIG. 16: with ($R_a$) and without (R) silk microarray embedded in tissues. As shown, the plotted parameter did not appear to depend on the absorption coefficient, but appeared to depend on the scattering coefficient consistently. The error in the calculated values was about 1%-2%. Because the free mean pathlength between consecutive scattering events is $1/\mu_s$, it can be assumed that photons reaching the depth of 1.5 mm were already diffused (on average 10-15 scattering events). Therefore it did not appear to require corrections even if the incident angle of the input light is changed. A more restricted (or asymmetric) FOV for the collected light may also be used.

In summary, as shown in FIG. 16, the experimental detected reflective increase (about 40% increase) by embedding silk microarray in mouse falls within the range obtained by MC simulation. As for the adipose tissue, the increased values detected in the experiment by embedding silk microarray in the tissue (~230%) are also close to the increase obtained by MC simulation.

What is claimed is:

1. A process for fabricating a silk reflector, comprising: replicating from a master pattern having a reflective element or an array of reflective elements onto a surface of a silk film, wherein the reflective element comprises a microprism.

2. The process of claim 1, further comprising: dispersing reflective particles in the silk film.

3. The process of claim 1, further comprising: adding at least one active agent to the silk film.

4. The process of claim 1, further comprising: functionalizing the silk film with an active group.

5. The process of claim 3, wherein the reflectivity of the silk reflector is modulated by the addition of the at least one active agent to the silk film.

6. A silk reflector comprising at least one layer of silk film, wherein a reflective element or an array of reflective elements is formed onto the surface of the silk film layer, and wherein the reflective element comprises a microprism.

7. The silk reflector of claim 6, further comprising reflective particles dispersed in the silk film.

8. The silk reflector of claim 6, further comprising at least one active agent in the silk film.

9. The silk reflector of claim 6, wherein the silk film is functionalized with an active group.

10. The silk reflector of claim 8, wherein the reflectivity of the silk reflector is modulated by addition of the active agent to the silk film.

11. The silk reflector of claim 8, wherein the reflectivity of the silk reflector is modulated by releasing the active agent from the silk film.

12. The silk reflector of claim 6, wherein the silk reflector is retroreflective.

13. The silk reflector of claim 6, characterized by an intensity of reflectivity enhanced by at least about 40% when the silk reflector is in an irregular scattering medium.

14. The silk of claim 13, wherein the scattering medium is ambient environment, water, liquids, suspensions, or gels, and wherein a thickness of the scattering medium blocking the silk reflector from a detection source is about 0-10 cm.

15. The silk reflector of claim 13, wherein the scattering medium is a tissue or organ, and wherein a thickness of the scattering medium blocking the silk reflector from a detection source is about 0-2 mm.

16. An implantable silk reflector having optical utility for in vivo operation, comprising:
    at least one layer of silk film having a reflective element or an array of reflective elements formed onto the surface of the silk layer, wherein the reflective element comprises a microprism, and wherein the silk reflector is biocompatible and bioresorbable.

17. The implantable silk reflector of claim 16, further comprising at least one active agent in the silk film.

18. The implantable silk reflector of claim 16, wherein the silk film is functionalized with an active group.

19. The implantable silk reflector of claim 16, wherein the reflectivity of the implantable silk reflector is modulated by addition of the active agent to the silk film or functionalization of the silk film with the active group.

20. The implantable silk reflector of claim 16, characterized by a reflectivity that is modulated when the implantable silk reflector is partially dissolved.

\* \* \* \* \*